United States Patent [19]

Bue-Valleskey et al.

[11] Patent Number: 5,716,975
[45] Date of Patent: Feb. 10, 1998

[54] COMPOUNDS USEFUL AS HYPOGLYCEMIC AGENTS AND FOR TREATING ALZHEIMER'S DISEASE

[75] Inventors: Juliana M. Bue-Valleskey, Indianapolis; David C. Hunden, Carmel; Charles D. Jones, Indianapolis; Jill A. Panetta, Zionsville; Walter N. Shaw, Indianapolis, all of Ind.

[73] Assignee: Eli Lilly and Company, Indianapolis, Ind.

[21] Appl. No.: 470,822

[22] Filed: Jun. 6, 1995

Related U.S. Application Data

[60] Division of Ser. No. 213,651, Mar. 16, 1994, Pat. No. 5,523,314, which is a continuation-in-part of Ser. No. 943,353, Sep. 10, 1992, abandoned.

[51] Int. Cl.$^6$ .................. C07D 277/31; A61K 31/125
[52] U.S. Cl. ............................. 514/369; 548/183
[58] Field of Search .......................... 548/183; 514/369

[56] References Cited

U.S. PATENT DOCUMENTS

| | | | |
|---|---|---|---|
| 4,287,200 | 9/1981 | Kawamatsu et al. | 424/270 |
| 4,376,777 | 3/1983 | Kawamatsu et al. | 424/270 |
| 4,387,101 | 6/1983 | Kawamatsu et al. | 424/270 |
| 4,461,902 | 7/1984 | Kawamatsu et al. | 548/183 |
| 4,464,382 | 8/1984 | Tanouchi et al. | 424/270 |
| 4,552,891 | 11/1985 | Ho et al. | 514/443 |
| 4,617,312 | 10/1986 | Schnur | 514/369 |
| 4,636,516 | 1/1987 | Kubo et al. | 514/365 |
| 4,703,052 | 10/1987 | Eggler et al. | 514/337 |
| 4,714,765 | 12/1987 | Ogawa et al. | 548/183 |
| 4,863,923 | 9/1989 | Ho et al. | 514/443 |
| 4,948,900 | 8/1990 | Iijima et al. | 548/183 |
| 4,971,996 | 11/1990 | Shiraishi | 514/521 |
| 4,997,948 | 3/1991 | Zask et al. | 548/183 |
| 5,116,855 | 5/1992 | Inoui et al. | 514/369 |
| 5,158,966 | 10/1992 | Lafferty | 514/369 |
| 5,208,250 | 5/1993 | Cetenko | 514/364 |
| 5,356,917 | 10/1994 | Panetta | 514/364 |

FOREIGN PATENT DOCUMENTS

| | | | |
|---|---|---|---|
| 045165 | 2/1982 | European Pat. Off. | C07D 277/36 |
| 193256 | 9/1986 | European Pat. Off. | C07D 417/12 |
| 208420 | 1/1987 | European Pat. Off. | C07D 417/12 |
| 211670 | 2/1987 | European Pat. Off. | A61K 31/39 |
| 212617 | 4/1987 | European Pat. Off. | C07C 57/38 |
| 237138 | 9/1987 | European Pat. Off. | C07D 417/04 |
| 343643 | 11/1989 | European Pat. Off. | A61K 31/41 |
| 391644 | 10/1990 | European Pat. Off. | C07D 277/14 |
| 398179 | 11/1990 | European Pat. Off. | C07D 277/36 |
| 434394 | 6/1991 | European Pat. Off. | C07D 277/14 |
| 449216 | 10/1991 | European Pat. Off. | C07D 277/14 |
| 569777 | 11/1993 | European Pat. Off. | C12Q 1/37 |
| 1038050 | 9/1958 | Germany | C07D 277/36 |
| 226617 | 9/1968 | U.S.S.R. | C07D 277/36 |
| 2249788 | 5/1992 | United Kingdom | C07D 277/36 |

OTHER PUBLICATIONS

Teuber et al., *Liebigs Ann. Chem.*, 757 (1978).
Katsumi et al., *Chem. Pharm. Bull.*, 34(4) 1619 (1986).
Chakrabarti et al., *Tetrahedron*, 2781 (1969).
Roggero et al., *Bull. De La Societe Chimique De France* 11, 4021 (1971).
Patent Abstracts of Japan, 11(232) (C–437) [2679] 1987, abstracting JP 62–45553.
Allan et al., *J. Org. Chem.*, 23, 112 (1958).
Fujita et al., *Diabetes* 32, 804 (1983).
Shoda et al., *Chem. Pharm. Bull.*, 30(10), 3563 (1982).
Shoda et al., *Chem. Pharm. Bull.*, 30(10), 3580 (1982).
Shoda et al., *Chem. Pharm. Bull.*, 32(6), 2267 (1984).
Tomisawa et al., *Chem. Pharm. Bull.*, 34(2), 701 (1986).
Isomura et al., *Chem. Pharm. Bull.*, 32(1), 152 (1984).
Patent Abstracts of Japan, 11(206) (C–433) [2653] 1987, abstracting JP 62–29570.
Derwent Abstracts, 87–076383/11, abstracting J6 2029–579A (1991).
Chemical Abstracts, vol. 116, No. 20983q (1992).
*Chemical Abstracts*, 69, No. 42531d (1968).
Agarwal et. al., *Curr Sci*, 49(12) 455 (1980).
Husain et al., *Acta Pharma. Jugoslav* 36(3) 311 (1986).
Derwent Abstracts 91–031957, abstracting JP–A–2 300,119, 1991.
Mohan et al., *Indian Drugs*, 21/3, 90 (1983).

*Primary Examiner*—Robert Gerstl
*Attorney, Agent, or Firm*—Arleen Palmberg; Douglas J. Taylor

[57] ABSTRACT

Provided are methods for treating hyperglycemia and Alzheimer's disease utilizing certain rhodanine derivatives. Certain of the rhodanine derivatives utilized in the instant methods are novel and, accordingly, such compounds and pharmaceutical formulations thereof are also provided.

16 Claims, No Drawings

COMPOUNDS USEFUL AS HYPOGLYCEMIC AGENTS AND FOR TREATING ALZHEIMER'S DISEASE

CROSS REFERENCE TO RELATED APPLICATIONS

This application is a division of application Ser. No. 08/213,651, filed Mar. 16, 1994, now U.S. Pat. No. 5,523,314, which is a Continuation in Part application of application Ser. No. 07/943,353 filed Sep. 10, 1992 abandoned.

BACKGROUND OF THE INVENTION

Diabetes mellitus is a systemic disease characterized by disorders in the metabolism of insulin, carbohydrates, fats and proteins, and in the structure and function of blood vessels. The primary symptom of acute diabetes is hyperglycemia, often accompanied by glucosuria, the presence in urine of large amounts of glucose, and polyuria, the excretion of large volumes of urine. Additional symptoms arise in chronic or long standing diabetes. These symptoms include degeneration of the walls of blood vessels. Although many different organs are affected by these vascular changes, the eyes and kidneys appear to be the most susceptible. As such, long-standing diabetes mellitus, even, when treated with insulin, is a leading cause of blindness.

There are two recognized types of diabetes. Type I diabetes is of juvenile onset, ketosis-prone, develops early in life with much more severe symptoms and has a near-certain prospect of later vascular involvement. Control of this type of diabetes is difficult and requires exogenous insulin administration. Type II diabetes mellitus is of adult onset, ketosis-resistant, develops later in life, is milder and has a more gradual onset.

One of the most significant advancements in the history of medical science came in 1922 when Banting and Best demonstrated the therapeutic effects of insulin in diabetic humans. However, even today, a clear picture of the basic biochemical defects of the disease is not known, and diabetes is still a serious health problem. It is believed that two percent of the United States' population is afflicted with some form of diabetes.

The introduction of orally effective hypoglycemic agents was an important development in the treatment of hyperglycemia by lowering blood glucose levels. Oral hypoglycemic agents are normally used in the treatment of adult onset diabetes.

A variety of biguanide and sulfonylurea derivatives have been used clinically as hypoglycemic agents. However, the biguanides tend to cause lactic acidosis and the sulfonylureas, though having good hypoglycemic activity, require great care during use because they frequently cause serious hypoglycemia and are most effective over a period of ten years.

In *Chemical & Pharmaceutical Bulletin*, 30, 3563 (1982), *Chemical & Pharmaceutical Bulletin*, 30, 3580 (1982) and *Chemical & Pharmaceutical Bulletin*, 32, 2267 (1984), reference is made to a variety of thiazolidinediones which have blood glucose and lipid lowering activities. Antidiabetic activity of ciglitazone was also reported in *Diabetes*, 32, 804 (1983). However, these compounds have proven difficult to use because of insufficient activities and/or serious toxicity problems.

Furthermore, Alzheimer's disease, a degenerative disorder of the human brain, continues to afflict more and more persons throughout the world. Such disease results in progressive mental deterioration manifested by memory loss, confusion, disorientation and the concomitant loss of enjoyment of life associated therewith. At the present time there is no scientifically recognized treatment for Alzheimer's disease. Because of this, and because of the debilitating effects of the disease, there continues to exist an urgent need for effective treatments.

The present invention relates to a series of hypoglycemic agents which are capable of lowering blood glucose levels in mammals. Accordingly, one object of the present invention is to provide compounds having excellent hypoglycemic activity. The hypoglycemic agents of the present invention are believed to have minimal toxicological effects. It is, therefore, believed that the compounds of the present invention may be very useful for treating diabetes.

The present invention also relates to a series of compounds having cathepsin inhibitory activity. As will be discussed more fully below, compounds capable of inhibiting cathepsin (and, in particular, cathepsin D) may be useful for treating Alzheimer's disease. Accordingly, a further object of the present invention is to provide compounds which can be used to treat Alzheimer's disease.

Other objects, features and advantages of the present invention will become apparent from the subsequent description and the appended claims.

SUMMARY OF THE INVENTION

The present invention provides a method of reducing blood glucose concentrations in mammals comprising administering a therapeutically effective amount of a compound of formula (I)

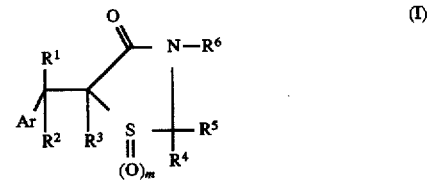

wherein:

Ar is (i) phenyl, (ii) phenyl substituted with from one to three substituents independently selected from $C_1$–$C_8$ alkyl, $C_1$–$C_8$ alkoxy, $C_1$–$C_8$ alkylthio, trifluoromethyl, $C_1$–$C_4$ alkylphenyl, phenyl, $NO_2$, F, Cl, hydroxy, phenoxy, $C_1$–$C_4$ alkyloxyphenyl, thiophenyl, $C_1$–$C_4$ alkylthiophenyl, —$COOR^7$, —$N(R^7)SO_2R^7$ or —$N(R^7)_2$, where each $R^7$ is independently hydrogen or $C_1$–$C_6$ alkyl, (iii) 1- or 2-naphthyl, (iv) 2- or 3-benzofuranyl, (v) 2- or 3-benzothiophenyl, (vi) 2-, or 3-thienyl, (vii) 2-, 3- or 4-pyridyl, (viii) 2- or 3-furanyl, (ix) 1,3-benzodioxanyl, (x) substituted 1,3-benzodioxanyl, (xi) quinolinyl, (xii) 2- or 3-indolyl or (xiii) N-substituted 2- or 3-indolyl;

$R^1$ is $C_1$–$C_6$ alkyl, $C_1$–$C_4$ alkylphenyl, hydrogen, phenyl or phenyl substituted with one or two substituents independently selected from Cl, Br, F, I, $C_1$–$C_4$ alkyl, $C_1$–$C_4$ alkoxy, hydroxy, trifluoromethyl, —$NH_2$, —NH ($C_1$–$C_4$ alkyl), —N($C_1$–$C_4$ alkyl)$_2$ or $C_1$–$C_4$ alkylthio;

$R^2$ and $R^3$ are each hydrogen or when taken together form a bond;

$R^4$ and $R^5$ are each hydrogen or when taken together are =S, or when one of $R^4$ and $R^5$ is hydrogen, the other is —$SCH_3$;

$R^6$ is hydrogen, $C_1$–$C_6$ alkyl, $C_3$–$C_8$ cycloalkyl, $C_2$–$C_6$ alkenyl, —$SO_2CH_3$, or —$(CH_2)_p$—Y where p is 0, 1, 2, or 3 and Y is cyano, —$OR^8$,

tetrazolyl, —NR$^{10}$R$^{11}$, —SH, C$_1$–C$_4$ alkylthio, or

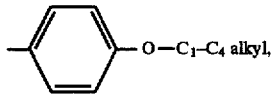

where R$^8$ is hydrogen, C$_1$–C$_4$ alkyl or

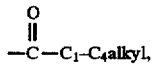

R$^9$ is hydrogen, C$_1$–C$_4$ alkyl, C$_1$–C$_4$ alkoxy, hydroxy or NH$_2$, and R$^{10}$ and R$^{11}$ are each independently hydrogen, C$_1$–C$_6$ alkyl, C$_2$–C$_6$ alkenyl, C$_2$–C$_6$ alkynyl, phenyl, C$_1$–C$_4$ alkylphenyl, —(CH$_2$)$_q$OH, —(CH$_2$)$_q$N(C$_1$–C$_4$ alkyl)$_2$, or —(CH$_2$)$_q$S(C$_1$–C$_4$ alkyl), where q is an integer from 1 to 6, both inclusive, or R$^{10}$ and R$^{11}$, taken together with the nitrogen atom to which they are attached, form a morpholinyl, piperidinyl, piperizinyl, or N-methylpiperazinyl ring; and m is 0, 1, or 2; with the provisos that Ar cannot be phenyl substituted solely with one chloro substituent at the 4-position of the phenyl ring;

Ar cannot be phenyl substituted with a COOH moiety at the 2-position of the phenyl ring;

when Ar is phenyl substituted with two ethoxy moieties at the 3- and 4-positions of the phenyl ring, R$^1$ must be hydrogen;

Ar cannot be phenyl substituted solely with two hydroxy substituents; and when R$^4$ and R$^5$ are each hydrogen, R$^6$ cannot be C$_1$–C$_6$ alkyl, or a pharmaceutically acceptable salt thereof, to a mammal in need of having its blood glucose concentration reduced.

The present invention also provides a method of treating Alzheimer's disease in a mammal suffering from or susceptible to such disease comprising administering a therapeutically effective amount of a compound of formula (Ia)

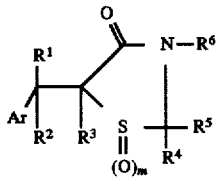
(Ia)

wherein:

Ar is (i) phenyl, (ii) phenyl substituted with from one to three substituents independently selected from C$_1$–C$_8$ alkyl, C$_1$–C$_8$ alkoxy, C$_1$–C$_8$ alkylthio, trifluoromethyl, C$_1$–C$_4$ alkylphenyl, phenyl, NO$_2$, F, Cl, hydroxy, phenoxy, C$_1$–C$_4$ alkyloxyphenyl, thiophenyl, C$_1$–C$_4$ alkylthiophenyl, —COOR$^7$, —N(R$^7$)SO$_2$R$^7$ or —N(R$^7$)$_2$, where each R$^7$ is independently hydrogen or C$_1$–C$_6$ alkyl or (iii) 1- or 2-naphthyl;

R$^1$ is C$_1$–C$_6$ alkyl, C$_1$–C$_4$ alkylphenyl, hydrogen, phenyl or phenyl substituted with one or two substituents independently selected from Cl, Br, F, I, C$_1$–C$_4$ alkyl, C$_1$–C$_4$ alkoxy, hydroxy, trifluoromethyl, —NH$_2$, —NH (C$_1$–C$_4$ alkyl), —N(C$_1$–C$_4$ alkyl)$_2$ or C$_1$–C$_4$ alkylthio;

R$^2$ and R$^3$ are each hydrogen or when taken together form a bond;

R$^4$ and R$^5$ are each hydrogen or when taken together are =S, or when one of R$^4$ and R$^5$ is hydrogen, the other is —SCH$_3$;

R$^6$ is hydrogen, C$_1$–C$_6$ alkyl, C$_3$–C$_8$ cycloalkyl, C$_2$–C$_6$ alkenyl, —SO$_2$CH$_3$, or —(CH$_2$)$_p$—Y where p is 0, 1, 2, or and Y is cyano, —OR$^8$,

tetrazolyl, —NR$^{10}$R$^{11}$, —SH, C$_1$–C$_4$ alkylthio, or

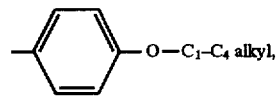

where R$^8$ is hydrogen, C$_1$–C$_4$ alkyl or

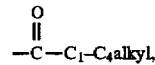

R$^9$ is hydrogen, C$_1$–C$_4$ alkyl, C$_1$–C$_4$ alkoxy, hydroxy or NH$_2$, and R$^{10}$ and R$^{11}$ are each independently hydrogen, C$_1$–C$_6$ alkyl, C$_2$–C$_6$ alkenyl, C$_2$–C$_6$ alkynyl, phenyl, C$_1$–C$_4$ alkylphenyl, —(CH$_2$)$_q$OH, —(CH$_2$)$_q$N (C$_1$–C$_4$ alkyl)$_2$, or —(CH$_2$)$_q$S(C$_1$–C$_4$ alkyl), where q is an integer from 1 to 6, both inclusive, or R$^{10}$ and R$^{11}$, taken together with the nitrogen atom to which they are attached, form a morpholinyl, piperidinyl, piperizinyl, or N-methylpiperazinyl ring; and m is 0, 1, or 2;

or a pharmaceutically acceptable salt thereof, to a mammal in need of such treatment.

Certain of the compounds which can be employed in the methods of the present invention are novel. As such, the present invention also provides novel compounds of the formula (II)

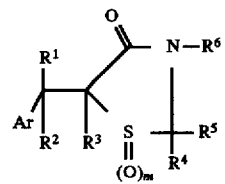
(II)

wherein:

Ar is (i) phenyl, (ii) phenyl substituted with from one to three substituents independently selected from C$_1$–C$_8$ alkyl, C$_1$–C$_8$ alkoxy, C$_1$–C$_8$ alkylthio, trifluoromethyl, C$_2$–C$_4$ alkylphenyl, NO$_2$, F, Cl, phenoxy, C$_1$–C$_4$ alkyloxyphenyl, thiophenyl, C$_1$–C$_4$ alkylthiophenyl, —COOR$^7$, —N(R$^7$)SO$_2$R$^7$ or —N(R$^7$)$_2$, where each R$^7$ is independently hydrogen or C$_1$–C$_6$ alkyl, (iii) 1- or 2-naphthyl, (iv) 2- or 3-benzofuranyl, (v) 2- or 3-benzothiophenyl, (vi) 2- or 3-thienyl, (vii) 2-, 3- or 4-pyridyl, (viii) 2- or 3-furanyl, (ix) 1,3-benzodioxanyl, (x) substituted 1,3-benzodioxanyl, (xi) quinolinyl, (xii) 2- or 3-indolyl or (xiii) N-substituted 2- or 3-indolyl;

R$^1$ is C$_1$–C$_6$ alkyl, C$_1$–C$_4$ alkylphenyl, hydrogen, phenyl or phenyl substituted with one or two substituents independently selected from Cl, Br, F, I, C$_1$–C$_4$ alkyl, C$_1$–C$_4$ alkoxy, hydroxy, trifluoromethyl, —NH$_2$, —NH (C$_1$–C$_4$ alkyl), —N(C$_1$–C$_4$ alkyl)$_2$ or C$_1$–C$_4$ alkylthio;

$R^2$ and $R^3$ are each hydrogen or when taken together form a bond;

$R^4$ and $R^5$ are each hydrogen or when taken together are =S, or when one of $R^4$ and $R^5$ is hydrogen, the other is —SCH$_3$;

$R^6$ is hydrogen, $C_1$–$C_6$ alkyl, $C_3$–$C_8$ cycloalkyl, $C_2$–$C_6$ alkenyl, —SO$_2$CH$_3$ or —(CH$_2$)$_p$—Y where p is 0, 1, 2, or 3 and Y is cyano OR$^8$,

tetrazolyl, —NR$^{10}$R$^{11}$, —SH, $C_1$–$C_4$ alkylthio or

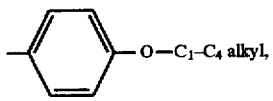

where $R^8$ is hydrogen, $C_1$–$C_4$ alkyl, or

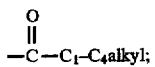

$R^9$ is hydrogen, $C_1$–$C_4$ alkyl or NH$_2$; and $R^{10}$ and $R^{11}$ are each independently hydrogen, $C_1$–$C_6$ alkyl, $C_2$–$C_6$ alkenyl, —(CH$_2$)$_q$OH, —(CH$_2$)$_q$N($C_1$–$C_4$ alkyl)$_2$, —(CH$_2$)$_q$S($C_1$–$C_4$ alkyl), $C_2$–$C_6$ alkynyl, phenyl, or $C_1$–$C_4$ alkylphenyl, where q is 1 to 6, both inclusive, or $R^{10}$ and $R^{11}$, taken together with the nitrogen atom to which they are attached, form a morpholinyl, piperidinyl, piperazinyl or N-methylpiperazinyl ring; and m is 0, 1, or 2;

with the provisos that when Ar is (i) phenyl, (ii) phenyl substituted with from one to three substituents selected from $C_1$–$C_8$ alkyl, $C_1$–$C_8$ alkoxy, F, Cl, trifluoromethyl, phenoxy, $C_1$–$C_4$ alkyloxyphenyl, $C_1$–$C_8$ alkylthio, NO$_2$, —N(R$^7$)$_2$ or —COOR$^7$, where each $R^7$ is independently hydrogen or $C_1$–$C_6$ alkyl, (iii) 1- or 2-naphthyl, (iv) 2- or 3-benzofuranyl, (v) 2- or 3-benzothiophenyl, (vi) 2- or 3-thienyl, (vii) 2- or 3-indolyl, (viii) 2- or 3-furanyl, (ix) quinolinyl or (x) 2-, 3- or 4-pyridyl; $R^1$ is hydrogen or $C_1$–$C_6$ alkyl; $R^2$ and $R^3$ taken together form a bond; m is 0; and $R^4$ and $R^5$ taken together are =S, $R^6$ must be other than hydrogen or $C_1$–$C_6$ alkyl;

when Ar is phenyl; $R^1$ is hydrogen, methyl or ethyl; $R^2$ and $R^3$ taken together form a bond; m is 0; $R^4$ and $R^5$ taken together are =S; $R^6$ must be other than phenyl or $C_1$–$C_4$ alkylphenyl;

Ar cannot be phenyl substituted solely with one chloro substituent at the 4-position of the phenyl ring;

when Ar is phenyl substituted with two ethoxy moieties at the 3- and 4-positions of the phenyl ring, $R^1$ must be hydrogen;

Ar cannot be phenyl substituted with a COOH moiety at the 2-position of the phenyl ring; and when $R^4$ and $R^5$ are each hydrogen $R^6$ cannot be $C_1$–$C_6$ alkyl, and the pharmaceutically acceptable salts thereof.

In addition to the genus of novel compounds described by formula II, above, certain other of the compounds which can be employed in the methods of the present invention also appear to be novel. These compounds, while structurally similar to compounds specifically known in the art (see, for example, European Patent Application Nos. 343643, 391644 and 39817 as well as U.S. Pat. No. 4,552,891), are not actually described in any of those patents or applications. As such, the present invention also encompasses the following novel compounds and their pharmaceutically acceptable salts:

5-[(2-nitrophenyl)methylene]-2-thioxo-4-thiazolidinone;
5-[(4-fluorophenyl)methylene]-2-thioxo-4-thiazolidinone;
5-[(2-thienyl)methylene]-2-thioxo-4-thiazolidinone;
5-[(2-furanyl)methylene]-2-thioxo-4-thiazolidinone;
5-[(3,4,5-trimethoxyphenyl)methylmethylene]-2-thioxo-4-thiazolidinone;
4-[(2-thioxo-4-thiazolidinone)methylene]benzoic acid;
5-[(3-hydroxy-4-nitrophenyl)methylene]-2-thioxo-4-thiazolidinone;
5-[(3-hydroxyphenyl)methylmethylene]-2-thioxo-4-thiazolidinone;
5-[(3-methoxy-4-pentoxyphenyl)methylene]-2-thioxo-4-thiazolidinone;
5-[(3-hydroxy-4-ethoxyphenyl)methylene]-2-thioxo-4-thiazolidinone;
5-[(4-pentoxyphenyl)methylene]-2-thioxo-4-thiazolidinone;
5-[(3-ethoxy-4-propoxyphenyl)methylene]-2-thioxo-4-thiazolidinone;
5-[(3-propoxy-4-ethoxyphenyl)methylene]-2-thioxo-4-thiazolidinone;
5-[(3,4-dipropoxyphenyl)methylene]-2-thioxo-4-thiazolidinone;
5-[[3-(methyloxyphenyl)phenyl]methylene]-2-thioxo-4-thiazolidinone;
5-[[3,5-bis(1,1-dimethylethyl)-4-methoxyphenyl]methylene]-2-thioxo-4-thiazolidinone;
5-[(3-ethoxy-4-hydroxy)phenyl]methylene]-2-thioxo-3-methyl-4-thiazolidinone;
5-[(3-ethoxy-4-hydroxyphenyl)methylene]-2-thioxo-3-dimethylamino-4-thiazolidinone
5-[(3,4-dipentoxyphenyl)methylene]-4-oxo-2-thioxo-3-thiazolidine acetic acid;
5-[[3,5-bis(1,1-dimethylethyl)-4-hydroxyphenyl] methylene]-4-oxo-2-thioxo-3-thiazolidine acetic acid;
5-[(3,5-dichloro-4-hydroxyphenyl)methylene]-2-thioxo-4-thiazolidinone;
5-[(3-ethoxy-4-butoxyphenyl)methylene]-2-thioxo-4-thiazolidinone;
5-[(3-ethoxy-4-methoxyphenyl)methylene]-2-thioxo-4-thiazolidinone;
5-[[3,5-bis(1-methylpropyl)-4-hydroxyphenyl]methylene]-4-oxo-2-thioxo-3-thiazolidine acetic acid;
5-[(4-butoxyphenyl)methylene]-2-thioxo-4-thiazolidinone;
5-[(3-methoxy-4-pentoxyphenyl)methylene]-2-thioxo-3-methyl-4-thiazolidinone;
5-[(3-methoxy-4-octoxyphenyl)methylene]-2-thioxo-4-thiazolidinone;
5-[(3,5-dimethoxy-4-pentoxyphenyl)methylene]-2-thioxo-4-thiazolidinone;
5-[[3-(1,1-dimethylethyl)-4-hydroxy-5-(methyl-thiophenyl)phenyl]methylene]-2-thioxo-4-thiazolidinone;
5-[[3-ethoxy-4-hydroxy-5-(methylthiophenyl)phenyl]methylene]-2-thioxo-4-thiazolidinone;
5-[[3-ethoxy-4-hydroxy-5-(methylthiophenyl)phenyl]methylene]-2-thioxo-3-methyl-4-thiazolidinone;
5-[[3-ethoxy-4-hydroxy-5-(methylthiophenyl)phenyl]methylene]-4-oxo-2-thioxo-3-thiazolidine acetic acid;
5-[(3-(1,1-dimethylethyl)-4-hydroxyphenyl]methylene]-2-thioxo-3-methyl-4-thiazolidinone.

Certain of the above compounds and, in particular, 5-[(4-pentoxyphenyl)methylene]-2-thioxo-4-thiazolidinone; 5-[

(3-propoxy-4-ethoxyphenyl)methylene]-2-thioxo-4-thiazolidinone; 5-[(3-ethoxy-4-butoxyphenyl)methylene]-2-thioxo-4-thiazolidinone; 5-[(4-butoxyphenyl)methylene]-2-thioxo-4-thiazolidinone; 5-[(3-methoxy-4-pentoxyphenyl)methylene]-2-thioxo-4-thiazolidinone; 5-[(3,5-bis(1,1-dimethylethyl)-4-hydroxyphenyl]methylene]-4-oxo-2-thioxo-3-thiazolidine acetic acid; and 5-[[3,5-bis(1-methylpropyl)-4-hydroxy-phenyl]methylene]-4-oxo-2-thioxo-3-thiazolidine acetic acid (especially the latter three compounds), appear to possess a surprising ability to lower blood glucose levels in mammals compared to structurally similar compounds known in the art. Because of such surprising activity, these compounds are particularly preferred compounds of the present invention.

In addition, 5-[[3-(1,1-dimethylethyl)-4-hydroxy-5-(methylthiophenyl)phenyl]methylene]-2-thioxo-4-thiazolidinone, 5-[(3,5-dichloro-4-hydroxyphenyl)methylene]-2-thioxo-4-thiazolidinone, 5-[(3-ethoxy-4-butoxyphenyl)methylene]-2-thioxo-4-thiazolidinone, 5-[[3-ethoxy-4-hydroxy-5-(methylthiophenyl)phenyl]methylene]-2-thioxo-4-thiazolidinone, 5-[[3-ethoxy-4-hydroxy-5-(methylthiophenyl)phenyl]methylene]-4-oxo-2-thioxo-3-thiazolidine acetic acid, 5-[(3-ethoxy-4-hydroxyphenyl)methylene]-2-thioxo-3-methyl-4-thiazolidinone, 5-[(3-ethoxy-4-hydroxyphenyl)methylene]-2-thioxo-3-dimethylamino-4-thiazolidinone, 5-[(3,4-dipentoxyphenyl)-methylene]-4-oxo-2-thioxo-3-thiazolidine acetic acid and 5-[[3-(1,1-dimethylethyl)-4-hydroxyphenyl]methylene-2-thioxo-3-methyl-4-thiazolidinone appear to possess a surprising ability to inhibit cathepsin D levels compared to structurally similar compounds known in the art. Because of such surprising activity, such compounds are also particularly preferred compounds of the present invention.

Finally, the present invention also provides pharmaceutical formulations comprising a compound of the present invention, or a pharmaceutically acceptable salt thereof, in combination with one or more pharmaceutically acceptable carriers, diluents or excipients therefor.

DETAILED DESCRIPTION OF THE INVENTION

As used herein, the term "$C_1$–$C_8$ alkyl" represents a straight or branched alkyl chain having from one to eight carbon atoms. Typical $C_1$–$C_8$ alkyl groups include methyl, ethyl, n-propyl, isopropyl, n-butyl, sec-butyl, isobutyl, t-butyl, n-pentyl, and the like. The term "$C_1$–$C_8$ alkyl" includes within its definition the terms "$C_1$–$C_4$ alkyl" and "$C_1$–$C_6$ alkyl".

"$C_1$–$C_4$ alkylphenyl" represents a straight or branched chain alkyl group having from one to four carbon atoms attached to a phenyl ring. Typical $C_1$–$C_4$ alkylphenyl groups include methylphenyl, ethylphenyl, n-propylphenyl, isopropylphenyl, n-butylphenyl, isobutylphenyl, and tert-butylphenyl.

The term "$C_1$–$C_4$ alkylthiophenyl" represents a straight or branched chain alkyl group having from one to four carbon atoms attached to a thiophenyl moiety. Typical $C_1$–$C_4$ alkylthiophenyl groups include methylthiophenyl, ethylthiophenyl, isobutylthiophenyl and the like.

In a similar fashion, the term "$C_1$–$C_4$ alkyloxyphenyl" represents a straight or branched chain alkyl group having from one to four carbon atoms attached to phenoxy moiety. Typical $C_1$–$C_4$ alkyloxyphenyl groups include methyloxyphenyl, ethyloxyphenyl, propyloxyphenyl and the like.

"$C_1$–$C_8$ alkoxy" represents a straight or branched alkyl chain having one to eight carbon atoms, which chain is attached to the remainder of the molecule by an oxygen atom. Typical $C_1$–$C_8$ alkoxy groups include methoxy, ethoxy, propoxy, isopropoxy, butoxy, isobutoxy, sec-butoxy, tert-butoxy, pentoxy, hexoxy, heptoxy, and the like. The term "$C_1$–$C_8$ alkoxy" includes within its definition the term "$C_1$–$C_4$ alkoxy".

"$C_1$–$C_8$ alkylthio" represents a straight or branched alkyl chain having one to eight carbon atoms, which chain is attached to the remainder of the molecule by a sulfur atom. Typical $C_1$–$C_8$ alkylthio groups include methylthio, ethylthio, propylthio, butylthio, tert-butylthio, octylthio and the like. The term "$C_1$–$C_8$ alkylthio" includes within its definition the term "$C_1$–$C_4$ alkylthio".

The term "$C_2$–$C_6$ alkenyl" refers to straight and branched chain radicals of two to six carbon atoms, both inclusive, having a double bond. As such, the term includes ethylene, propylene, 1-butene, 2-butene, 2-methyl-1-propene, 1-pentene, 2-methyl-2-butene and the like.

The term "$C_2$–$C_6$ alkynyl" refers to straight and branched chain radicals of two to six carbon atoms, both inclusive, having a triple bond. As such, the term includes acetylene, propyne, 1-butyne, 2-hexyne, 1-pentyne, 3-ethyl-1-butyne and the like.

The term "$C_3$–$C_8$ cycloalkyl" refers to saturated alicyclic rings of three to eight carbon atoms, both inclusive, such as cyclopropyl, methylcyclopropyl, cyclobutyl, cyclopentyl, cyclohexyl, cyclooctyl and the like.

The terms "1,3-benzodioxanyl" and "substituted 1,3-benzodioxanyl" refer to structures of the formulae

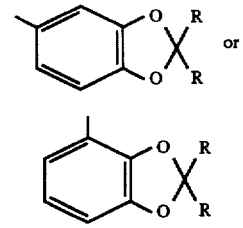

where each R is independently hydrogen or $C_1$–$C_4$ alkyl.

"Quinolinyl" refers to a quinoline ring system which is attached to the rest of the molecule at the 4, 5, 6, 7 or 8 position of such ring system.

"N-substituted 2- or 3-indolyl" refers to a 2- or 3-indolyl ring system substituted on the nitrogen atom of that ring system with a $C_1$–$C_6$ alkyl, $C_1$–$C_4$ alkylphenyl, or $C_3$–$C_8$ cycloalkyl group.

The term "pharmaceutically acceptable salts" refers to salts of the compounds of the above formulae which are substantially non-toxic to living organisms. Typical pharmaceutically acceptable salts include those salts prepared by reaction of the compounds of the above formulae with a pharmaceutically acceptable mineral or organic acid, or a pharmaceutically acceptable alkali metal or organic base, depending on the types of substituents present on the compounds of the formulae.

Examples of pharmaceutically acceptable mineral acids which may be used to prepare pharmaceutically acceptable salts include hydrochloric acid, phosphoric acid, sulfuric acid, hydrobromic acid, hydroiodic acid, phosphorous acid and the like. Examples of pharmaceutically acceptable organic acids which may be used to prepare pharmaceutically acceptable salts include aliphatic mono and dicarboxylic acids, oxalic acid, carbonic acid, citric acid, succinic acid, phenyl-substituted alkanoic acids, aliphatic and aromatic sulfonic acids and the like. Such pharmaceutically acceptable salts prepared from mineral or organic acids thus include hydrochloride, hydrobromide, nitrate, sulfate, pyrosulfate, bisulfate, sulfite, bisulfite, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like.

Many compounds of formulae I, Ia or II which contain a carboxy, carbonyl, hydroxy or sulfoxide group may be converted to a pharmaceutically acceptable salt by reaction with a pharmaceutically acceptable alkali metal or organic base. Examples of pharmaceutically acceptable organic bases which may be used to prepare pharmaceutically acceptable salts include ammonia, amines such as triethanolamine, triethylamine, ethylamine, and the like. Examples of pharmaceutically acceptable alkali metal bases included compounds of the general formula $MOR^{13}$, where M represents an alkali metal atom, e.g. sodium, potassium, or lithium, and $R^{13}$ represents hydrogen or $C_1$–$C_4$ alkyl.

It should be recognized that the particular anion or cation forming a part of any salt of this invention is not critical, so long as the salt, as a whole, is pharmacologically acceptable and as long as the anion or cationic moiety does not contribute undesired qualities.

A preferred genus of compounds useful in the instantly claimed method of reducing blood glucose concentrations includes those compounds wherein Ar, $R^1$, $R^2$, $R^3$, m, $R^4$, and $R^5$ are as set forth for formula I, and $R^6$ is hydrogen, $C_1$–$C_6$ alkyl, $C_3$–$C_8$ cycloalkyl, $C_2$–$C_6$ alkenyl, —$SO_2CH_3$ or —$(CH_2)_p$—Y where p is 0, 1, 2, or 3 and Y is cyano, —$OR^8$,

tetrazolyl, $NR^{10}R^{11}$, —SH, —S($C_1$–$C_4$ alkyl), or

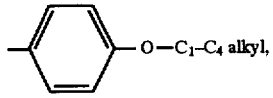

where $R^8$ is hydrogen, $C_1$–$C_4$ alkyl, or

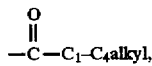

$R^9$ is hydrogen, $C_1$–$C_4$ alkyl, or $NH_2$; and $R^{10}$ and $R^{11}$ are each independently hydrogen, $C_1$–$C_6$ alkyl, $C_2$–$C_6$ alkenyl, $C_2$–$C_6$ alkynyl, phenyl, $C_1$–$C_4$ alkylphenyl, —$(CH_2)_qOH$, —$(CH_2)_qN(C_1$–$C_4$ alkyl$)_2$, or —$(CH_2)_qS(C_1$–$C_4$ alkyl) where q is 1 to 6, both inclusive, or $R^{10}$ and $R^{11}$, taken together with the nitrogen atom to which they are attached, form a morpholinyl, piperidinyl, piperazinyl, or N-methylpiperazinyl ring.

Of this preferred genus, those compounds in which m is 0 are more preferred.

Of this more preferred genus, those compounds in which $R^4$ and $R^5$ taken together are =S are even more preferred.

Of this even more preferred genus, those compounds in which $R^1$ is hydrogen are especially preferred.

Of this especially preferred genus, those compounds in which $R^6$ is hydrogen, $C_1$–$C_6$ alkyl, $C_2$–$C_6$ alkenyl, or —$(CH_2)_p$—Y where p is 0, 1, 2, or 3 and Y is —$OR^8$,

—$NR^{10}R^{11}$, or $C_1$–$C_4$ alkylthio where $R^8$ is hydrogen, $C_1$–$C_4$ alkyl or

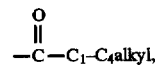

$R^9$ is hydrogen, $C_1$–$C_4$ alkyl or $NH_2$; and $R^{10}$ and $R^{11}$ are each independently hydrogen, $C_1$–$C_6$ alkyl, $C_2$–$C_6$ alkenyl, $C_2$–$C_6$ alkynyl, phenyl, or $C_1$–$C_4$ alkylphenyl are particularly preferred.

Of this particularly preferred genus, those compounds in which $R^6$ is hydrogen, $C_1$–$C_6$ alkyl, or $C_2$–$C_6$ alkenyl are more particularly preferred.

of this more particularly preferred genus, those compounds in which Ar is (i) phenyl, (ii) phenyl substituted with from one to three substituents independently selected from $C_1$–$C_8$ alkyl, $C_1$–$C_8$ alkoxy, $C_1$–$C_8$ alkylthio, trifluoromethyl, $C_1$–$C_4$ alkylphenyl, phenyl, $NO_2$, F, Cl, hydroxy, phenoxy, $C_1$–$C_4$ alkyloxyphenyl, thiophenyl, $C_1$–$C_4$ alkylthiophenyl, —$COOR^7$, —$N(R^7)SO_2R^7$ or —$N(R^7)_2$, where each $R^7$ is independently hydrogen or $C_1$–$C_6$ alkyl, (iii) 2-, 3- or 4-pyridyl, or (iv) 2- or 3-furanyl are substantially preferred.

Of this substantially preferred genus, those compounds wherein Ar is phenyl substituted with from one to three substituents independently selected from $C_1$–$C_8$ alkyl, $C_1$–$C_8$ alkoxy, $C_1$–$C_4$ alkylphenyl, phenyl, $NO_2$, F, Cl, hydroxy, phenoxy, $C_1$–$C_4$ alkylthiophenyl, —$COOR^7$ or —$N(R^7)SO_2R^7$, where each $R^7$ is independently hydrogen or $C_1$–$C_6$ alkyl, are more substantially preferred.

Of this more substantially preferred genus, those compounds wherein Ar is phenyl substituted with from one to three substituents independently selected from $C_1$–$C_8$ alkyl (especially $C_1$–$C_4$ alkyl), $C_1$–$C_8$ alkoxy (especially $C_1$–$C_6$ alkoxy), or hydroxy are even more substantially preferred.

The most preferred compounds which may be employed in the method of reducing blood glucose concentrations of the present invention include 5-[(3,4-diethoxyphenyl) methylene]-2-thioxo-4-thiazolidinone; 5-[(3-methoxy-4-butoxyphenyl)methylene]-2-thioxo-4-thiazolidinone; 5-[(3-methoxy-4-pentoxy-phenyl)methylene]-2-thioxo-4-thiazolidinone; 5-[(3-methoxy-4-pentoxyphenyl)methylene] -2-thioxo-4-thiazolidinone, sodium salt; 5-[(3-methoxy-4-pentoxyphenyl)methyl]-2-thioxo-4-thiazolidinone; 5[[3,5-bis(1,1-dimethylethyl)-4-hydroxyphenyl]methylene]-2-thioxo-4-thiazolidinone; 5[(3,5-dimethyl-4-hydroxyphenyl) methylene]-2-thioxo-4-thiazolidinone and 5-[(3,5-dimethoxy-4-hydroxyphenyl)methylene]-2-thioxo-4-thiazolidinone.

A preferred genus of compounds useful in the instantly claimed method of treating Alzheimer's disease includes those compounds wherein Ar, $R^1$, $R^2$, $R^3$, m, $R^4$ and $R^5$ are as set forth for formula Ia, and $R^6$ is hydrogen, $C_1$–$C_6$ alkyl or —$(CH_2)_pY$ where p is 0, 1, 2 or 3 and Y is

where $R^9$ is hydrogen, $C_1$–$C_4$ alkoxy or hydroxy, or —$NR^{10}R^{11}$ where $R^{10}$ and $R^{11}$ are each independently hydrogen, $C_1$–$C_6$ alkyl, phenyl or $C_1$–$C_4$ alkylphenyl.

Of this preferred genus, those compounds in which m is 0 are more preferred.

Of this more preferred genus, those compounds in which $R^4$ and $R^5$ taken together are =S are even more preferred.

Of this even more preferred genus, those compounds in which $R^2$ and $R^3$ taken together form a bond are especially preferred.

Of this especially preferred genus, those compounds in which Ar is phenyl substituted with from one to three substituents independently selected from $C_1$–$C_8$ alkyl, $C_1$–$C_8$ alkoxy, $C_1$–$C_8$ alkylthio, trifluoromethyl, $C_1$–$C_4$ alkylphenyl, phenyl, $NO_2$, F, Cl, hydroxy, phenoxy, $C_1$–$C_4$ alkyloxyphenyl, thiophenyl, $C_1$–$C_4$ alkylthiophenyl, —COOR$^7$, —N(R$^7$)SO$_2$R$^7$ or —N(R$^7$)$_2$, where each R$^7$ is independently hydrogen or $C_1$–$C_4$ alkyl, are particularly preferred.

Of this particularly preferred genus, those compounds in which R$^1$ is hydrogen are more particularly preferred.

Of this more particularly preferred genus, those compounds in which Ar is phenyl substituted with from one to three substituents independently selected from phenoxy, phenyl, $C_1$–$C_8$ alkoxy, $C_1$–$C_8$ alkyl (especially $C_1$–$C_4$ alkyl), hydroxy, Cl, F, $C_1$–$C_4$ alkylthiophenyl, $C_1$–$C_4$ alkyloxyphenyl, —N(R$^7$)SO$_2$R$^7$ and —N(R$^7$)$_2$, where each R$^7$ is independently hydrogen or $C_1$–$C_4$ alkyl, are substantially preferred.

The most preferred compounds which may be employed in the method of treating Alzheimer's disease of the present invention include 5-[(4-phenoxyphenyl)methylene]-2-thioxo-4-thiazolidinone; 5-[(3-phenoxyphenyl)methylene]-2-thioxo-4-thiazolidinone; 5-[[(1,1'-biphenyl)-4-yl]methylene]-2-thioxo-4-thiazolidinone; 5-[(3-methoxy-4-hexoxyphenyl)methylene]-2-thioxo-4-thiazolidinone; 5-[(3-methoxy-4-heptoxyphenyl)methylene]-2-thioxo-4-thiazolidinone; 5-[(3-methoxy-4-octoxyphenyl)methylene]-2-thioxo-4-thiazolidinone; 5-[[3,5-bis(1,1-dimethylethyl)-4-hydroxyphenyl]methylene]-2-thioxo-4-thiazolidinone; 5-[(3,5-dichloro-4-hydroxyphenyl)methylene]-2-thioxo-4-thiazolidinone; 5-[[3-(1,1-dimethylethyl)-4-hydroxy-5-(methylthiophenyl)phenyl]methylene]-2-thioxo-4-thiazolidinone; 5-[(3-methoxy-4-heptoxyphenyl)methylene]-2-thioxo-3-dimethylamino-4-thiazolidinone; 5-[(3-ethoxy-4-hydroxyphenyl)methylene]-2-thioxo-4-thiazolidinone; 5-[(3-ethoxy-4-butoxyphenyl)methylene]-2-thioxo-4-thiazolidinone; 5-[[3-ethoxy-4-hydroxy-5-(methylthiophenyl)phenyl]methylene]-2-thioxo-4-thiazolidinone; 5-[[3-ethoxy-4-hydroxy-5-(methylthiophenyl)phenyl]methylene]-4-oxo-2-thioxo-3-thiazolidine acetic acid; 5-[[3-(methyloxy-phenyl)phenyl]methylene]-2-thioxo-4-thiazolidinone; 5-[(3-ethoxy-4-hydroxyphenyl)methylene]-2-thioxo-3-methyl-4-thiazolidinone; 5-[(3-ethoxy-4-hydroxyphenyl)methylene]-2-thioxo-3-dimethylamino-4-thiazolidinone; 5-[(3,4-dipentoxyphenyl)methylene]-4-oxo-2-thioxo-3-thiazolidine acetic acid; 5-[[3-(1,1-dimethylethyl)-4-hydroxyphenyl]methylene]-2-thioxo-3-methyl-4-thiazolidinone; and 5-[[4-(dimethylamino)phenyl]methylene]-2-thioxo-4-thiazolidinone.

A preferred genus of compounds of the present invention includes those compounds wherein Ar, R$^1$, R$^2$, R$^3$, R$^4$, R$^5$ and R$^6$ are as set forth for Formula II, and m is 0. Of this preferred genus, those compounds in which R$^4$ and R$^5$ taken together are =S are more preferred. Of this more preferred genus, those compounds in which R$^2$ and R$^3$ taken together form a bond are especially preferred.

Of this especially preferred genus, those compounds in which R$^6$ is hydrogen, $C_1$–$C_6$ alkyl, $C_2$–$C_6$ alkenyl, or —(CH$_2$)$_p$—Y where p is 0, 1, 2, or 3 and Y is —OR$^8$,

—NR$^{10}$R$^{11}$, or $C_1$–$C_4$ alkylthio, where R$^8$ is hydrogen, $C_1$–$C_4$ alkyl or

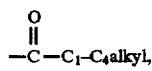

R$^9$ is hydrogen, $C_1$–$C_4$ alkyl or NH$_2$; and R$^{10}$ and R$^{11}$ are each independently hydrogen, $C_1$–$C_6$ alkyl, $C_2$–$C_6$ alkenyl, $C_2$–$C_6$ alkynyl, phenyl, or $C_1$–$C_4$ alkylphenyl are particularly preferred.

Of this particularly preferred genus, those compounds in which R$^6$ is hydrogen, $C_1$–$C_6$ alkyl, $C_2$–$C_6$ alkenyl or —NR$^{10}$R$^{11}$ where R$^{10}$ and R$^{11}$ are independently $C_1$–$C_6$ alkyl are more particularly preferred. Of this more particularly preferred genus, those compounds in which R$^1$ is hydrogen or phenyl are even more particularly preferred.

Of this even more particularly preferred genus, those compounds in which Ar is (i) phenyl, (ii) phenyl substituted with from one to three substituents independently selected from $C_1$–$C_8$ alkyl, $C_1$–$C_8$ alkoxy, $C_1$–$C_8$ alkylthio, trifluoromethyl, $C_2$–$C_4$ alkylphenyl, NO$_2$, F, Cl, phenoxy, $C_1$–$C_4$ alkoxyphenyl, thiophenyl, $C_1$–$C_4$ alkylthiophenyl, —COOR$^7$, —N(R$^7$)SO$_2$R$^7$ or —N(R$^7$)$_2$, where each R$^7$ is independently hydrogen or $C_1$–$C_6$ alkyl, (iii) 1,3-benzodioxanyl, (iv) substituted 1,3-benzodioxanyl or (v) quinolinyl are substantially preferred compounds.

Of this substantially preferred genus, those compounds wherein Ar is (i) phenyl substituted with from one to three of phenoxy, $C_1$–$C_8$ alkoxy, $C_1$–$C_4$ alkyloxyphenyl or —N(R$^7$)SO$_2$R$^7$, where each R$^7$ is hydrogen or $C_1$–$C_6$ alkyl or (ii) 1,3-benzodioxanyl are more substantially preferred.

Certain preferred compounds of the present invention include 5-(diphenylmethylene)-2-thioxo-4-thiazolidinone; 5-[(1,3-benzodioxol-5-yl)methylene)-2-thioxo-4-thiazolidinone; 5-[(4-phenoxyphenyl)methylene]-2-thioxo-4-thiazolidinone; 5-[(3-methoxy-4-heptoxyphenyl)methylene]-3-amino-2-thioxo-4-thiazolidinone; 5-[(3-methoxy-4-heptoxyphenyl)methylene]-3-dimethylamino-2-thioxo-4-thiazolidinone; 5-[(3,4-diheptoxyphenyl)methylene]-2-thioxo-3-dimethylamino-4-thiazolidinone; 5-[(3,4-dibutoxyphenyl)methylene]-2-thioxo-3-dimethylamino-4-thiazolidinone; 5-[(3-methoxy-4-heptoxyphenyl)methylene]-2-thioxo-3-(2-propenyl)-4-thiazolidinone; 5-[(3-methanesulfonamidophenyl)methylene]-4-oxo-2-thioxo-3-thiazolidine acetic acid; 5-[[3-(methyloxyphenyl)phenyl]methylene]-2-thioxo-4-thiazolidinone; 5-[(3-methoxy-4-heptoxyphenyl)methylene]-2-thioxo-3-dimethylamino-4-thiazolidinone; and 5-[(3-methanesulfonamidophenyl)methylene]-2-thioxo-4-thiazolidinone.

An alternative preferred genus of compounds of the present invention includes those compounds wherein Ar, R$^1$, R$^2$, R$^3$, R$^4$, R$^5$, and m are as defined for formula II, and R$^6$ is $C_3$–$C_8$ cycloalkyl, $C_2$–$C_6$ alkenyl, —SO$_2$CH$_3$ or —(CH$_2$)$_p$—Y where p is 0, 1, 2, or 3 and Y is cyano, —OR$^8$,

tetrazolyl, —NR$^{10}$R$^{11}$, —SH, $C_1$–$C_4$ alkylthio, or

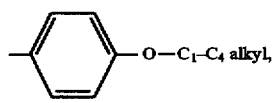

where R$^8$ is hydrogen, $C_1$–$C_4$ alkyl, or

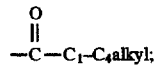

R$^9$ is hydrogen, $C_1$–$C_4$ alkyl, or NH$_2$; and R$^{10}$ and R$^{11}$ are each independently hydrogen, $C_1$–$C_6$ alkyl, $C_2$–$C_6$ alkenyl, $C_2$–$C_6$ alkynyl, phenyl, $C_1$–$C_4$ alkylphenyl, —(CH$_2$)$_q$OH, —(CH$_2$)$_q$N($C_1$–$C_4$ alkyl)$_2$, or —(CH$_2$)$_q$S($C_1$–$C_4$ alkyl) where q is 1 to 6, both inclusive, or R$^{10}$ and R$^{11}$, taken together with the nitrogen atom to which they are attached, form a morpholinyl, piperidinyl, piperazinyl, or N-methylpiperazinyl ring.

Of this preferred genus, those compounds in which m is 0 are more preferred.

Of this more preferred genus, those compounds in which $R^4$ and $R^5$ taken together are =S are even more preferred.

Of this even more preferred genus, those compounds in which $R^2$ and $R^3$ taken together form a bond are especially preferred Of this especially preferred genus, those compounds in which $R^6$ is $C_2-C_6$ alkenyl, or —$(CH_2)_p$—Y where p is 0, 1, 2, or 3 and Y is —$OR^8$,

—$NR^{10}R^{11}$, or $C_1-C_4$ alkylthio, where $R^8$ is hydrogen, $C_1-C_4$ alkyl or

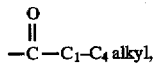

$R^9$ is hydrogen, $C_1-C_4$ alkyl or $NH_2$; and $R^{10}$ and $R^{11}$ are each independently hydrogen, $C_1-C_6$ alkyl, $C_2-C_6$ alkenyl, $C_2-C_6$ alkynyl, phenyl, or $C_1-C_4$ alkylphenyl are particularly preferred.

Of this particularly preferred genus, those compounds wherein $R^1$ is hydrogen or phenyl are more particularly preferred.

Of this more particularly preferred genus, those compounds in which Ar is (i) phenyl, (ii) phenyl substituted with from one to three substituents independently selected from $C_1-C_8$ alkyl, $C_1-C_8$ alkoxy, $C_1-C_8$ alkylthio, trifluoromethyl, $C_2-C_4$ alkylphenyl, $NO_2$, F, Cl, phenoxy, $C_1-C_4$ alkoxyphenyl, thiophenyl, $C_1-C_4$ alkylthiophenyl, —$COOR^7$, —$N(R^7)SO_2R^7$ or —$N(R^7)_2$, where each $R^7$ is independently hydrogen or $C_1-C_6$ alkyl (iii) 2-, 3- or 4-pyridyl, or (iv) 2- or 3-furanyl are even more particularly preferred.

Of this even more particularly preferred genus, those compounds wherein Ar is phenyl substituted with from one to three substituents independently selected from $C_1-C_8$ alkyl, $C_1-C_8$ alkoxy, $C_1-C_8$ alkylthio, trifluoromethyl, $C_2-C_4$ alkylphenyl, $NO_2$, F, Cl, phenoxy, $C_1-C_4$ alkoxyphenyl, thiophenyl, $C_1-C_4$ alkylthiophenyl, —$COOR^7$, —$N(R^7)SO_2R^7$ or —$N(R^7)_2$, where each $R^7$ is independently hydrogen or $C_1-C_6$ alkyl, are substantially preferred.

Of this substantially preferred genus, those compounds wherein Ar is phenyl substituted with from one to three substituents independently selected from $C_1-C_8$ alkyl or $C_1-C_8$ alkoxy are most preferred.

The present invention also encompasses formulations comprising a compound of the present invention in combination with a pharmaceutically acceptable carrier, diluent, or excipient therefor. Preferred formulations of the present invention are those formulations which contain a preferred compound or genus of compounds of the present invention, as described above.

The compounds of the present invention, as well as the compounds employed in the methods of the present invention, can, typically, be prepared by methods well known to one skilled in the art of organic chemistry. For example, such compounds may be prepared by condensation of rhodanine, or an appropriately substituted rhodanine derivative, with an appropriately substituted aromatic aldehyde or aldehyde derivative such as a mono or disubstituted imine of the formula

Such reaction is illustrated utilizing an appropriately substituted aromatic aldehyde as follows

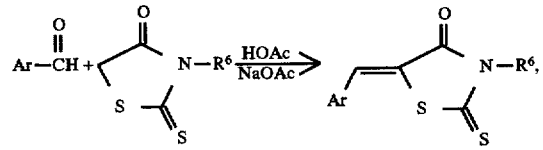

where Ar and $R^6$ are as defined in formulae I, Ia and II.

Compounds of the present invention (as well as those compounds employed in the methods of the present invention) wherein $R^2$ and $R^3$ are hydrogen, or when taken together form a bond, and $R^4$ and $R^5$ are each hydrogen can be prepared by subjecting the compound wherein $R^4$ and $R^5$ taken together form =S to catalytic hydrogenation. The relative proportions of compound obtained ($R^2$, $R^3$, $R^4$ and $R^5$ all hydrogen vs. $R^2$ and $R^3$ taken together form a bond and $R^4$ and $R^5$ are hydrogen) depends upon the temperature, pressure, and duration of hydrogenation, the solvent employed and the particular catalyst used. Alternatively, the above transformations may be accomplished by heating the compounds wherein $R^4$ and $R^5$ taken together are =S and $R^2$ and $R^3$ taken together are a double bond in a mixture of hydrochloric acid and an alcohol, such as ethanol, in the presence of zinc. Reduction of the thione without affecting the benzylic double bond may be accomplished by heating the thione with a reducing agent such as tri-n-butyl tin hydride in a non-reactive solvent, such as toluene, and preferably in the presence of a free radical initiator, such as azobisisobutyronitrile. However, for such reduction to work, an N-substituted rhodanine substrate must be employed.

The transformation of compounds wherein $R^2$ and $R^3$ taken together form a bond and $R^4$ and $R^5$ taken together are =S to those compounds wherein $R^2$ and $R^3$ are both hydrogen while $R^4$ and $R^5$ remain unchanged may be accomplished by treating the unsaturated compound with a dihydropyridine, such as diethyl 2,6-dimethyl-1,4-dihydro-3,5-pyridine dicarboxylate in the presence of silica gel. The reaction is best carried out in the presence of a nonreactive solvent such as benzene or toluene, preferably under an inert atmosphere. The reaction may be accomplished at temperatures from about 25° C. up to the reflux temperature of the mixture. At the preferred temperature of approximately 80° C., the reaction is essentially complete after about 12–18 hours.

Compounds of formulae I, Ia or II wherein $R^1$ is $C_1-C_6$ alkyl, phenyl, a substituted phenyl of the type described above, or $C_1-C_4$ alkylphenyl may be prepared by conventional Friedel-Crafts acylation of an appropriately substituted aromatic compound with an acyl halide of the formula $R^1$—C(O)—X, wherein $R^1$ is as defined in formulae I or II and X is chloro, fluoro, bromo or iodo. The resulting aromatic ketone is then condensed with rhodanine, or an appropriately substituted rhodanine derivative.

The compounds of the present invention (as well as the compounds employed in the methods of the present invention) allow various $R^6$ substituents. These $R^6$ substituents can be prepared as follows.

Compounds of formulae I, Ia and II wherein $R^6$ is hydrogen, $C_1-C_6$ alkyl, $C_3-C_8$ cycloalkyl or —$(CH_2)_p$—Y where p is as defined for formulae I, Ia and II and Y is cyano, or $NR^{10}R^{11}$ where $R^{10}$ and $R^{11}$ are each independently hydrogen or $C_1-C_6$ alkyl may be prepared using the method set forth in the above reaction scheme. Alternatively, rhodanine may be used for condensation with an aldehyde or aldehyde derivative forming those species wherein $R^6$ is hydrogen, followed by alkylation or acylation with the appropriate $R^6$-containing halide. The alkylation or acylation is usually accomplished in an inert solvent such as tetrahydrofuran or dimethylformamide and in the presence of a strong base such as sodium hydride.

Alternatively, compounds of formulae I, Ia and II wherein $R^6$ is $-(CH_2)_p-Y$ where Y is cyano may be prepared by treating the non-cyanated analog with a halo-substituted aliphatic nitrile. From this cyano derivative the tetrazolyl is prepared as by treatment with tri-N-butyl tin azide in, for example, ethylene glycol dimethyl ether.

Compounds of formulae I, Ia and II wherein $R^6$ is $-(CH_2)_p-Y$ (p=0) and Y is $NR^{10}R^{11}$, where $R^{10}$ and $R^{11}$ are as defined in formulae I, Ia and II, may also be prepared by employing an appropriately substituted hydrazine. In this reaction sequence, benzaldehyde is reacted with an appropriately substituted hydrazine, in an alcoholic solvent, yielding III. An appropriately substituted alkyl halide is then reacted with III, in the presence of triethylamine and acetonitrile, to provide IV, which is then further reacted with hydrazine to yield the $R^{10}$, $R^{11}$ hydrazine V. Compound V may alternatively be prepared by the reduction of a nitroso-$R^{10}R^{11}$ amine using zinc dust and acetic acid or aluminum and a strong base. The $R^{10}$, $R^{11}$ hydrazine is then treated with carbon disulfide, chloroacetic acid and triethylamine to provide intermediate VI. Condensation of VI with an appropriately substituted aromatic aldehyde or aldehyde derivative yields the desired product, as represented by the following reaction scheme.

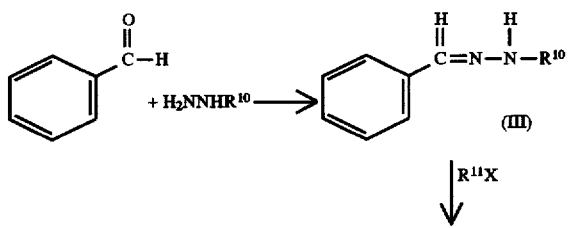

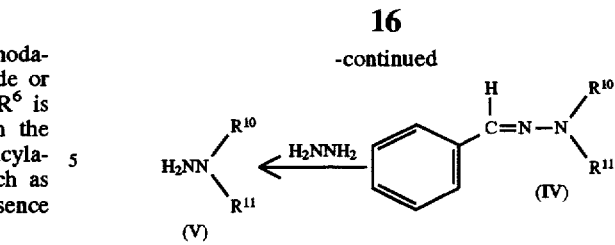

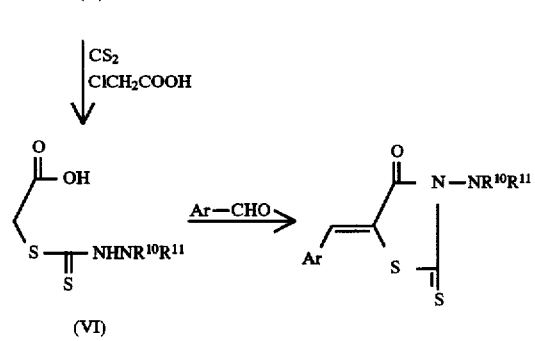

Furthermore, the thione portion of the compound produced above may be reduced by treatment with a reducing agent such as tri-n-butyltin hydride in an inert solvent such as toluene, preferably in the presence of a free radical initiator such as azobisisobutyronitrile. Preparation of compounds wherein one of $R^{10}$ and $R^{11}$ is hydrogen may be effected before or after reduction of the thione, as desired, by heating the disubstituted compound in a mixture of ethanol/water in the presence of a catalyst such as a rhodium catalyst.

Compounds of formulae I, Ia and II wherein $R^6$ is $-(CH_2)_p-Y$ and Y is $OR^8$ or $NR^{10}R^{11}$ (where $R^8$ is hydrogen, acetyl or tosyl and $R^{10}$ and $R^{11}$ are each independently hydrogen or $C_1-C_6$ alkyl) may also be prepared according to the following reaction scheme:

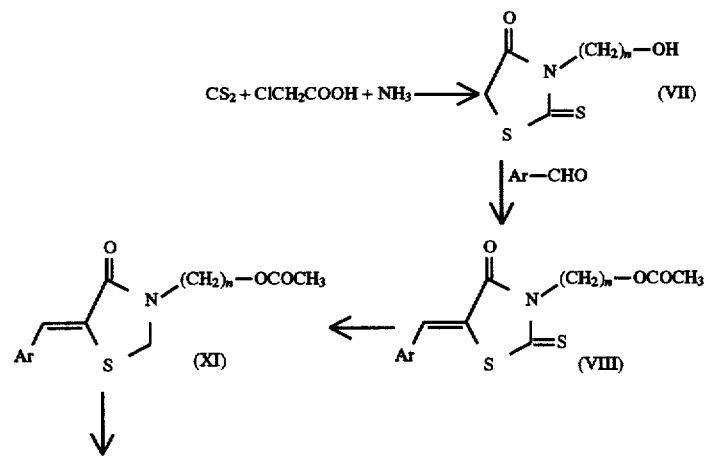

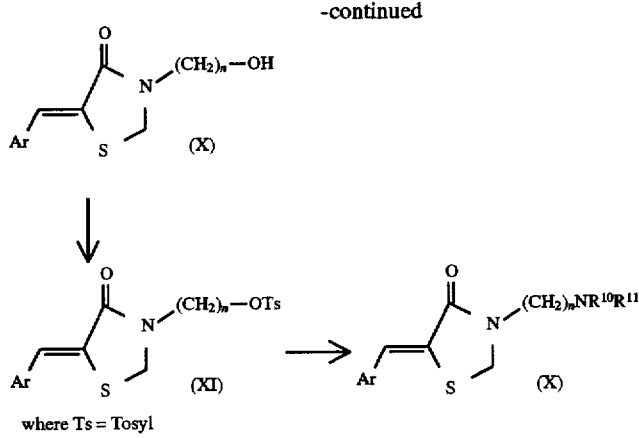

where Ts = Tosyl

A hydroxyalkyl rhodanine is prepared by condensing carbon disulfide, chloroacetic acid, and the appropriate hydroxyalkylamine by standard techniques. When condensed with the appropriately substituted aromatic aldehyde (or aldehyde derivative), as described above, the resulting product is the condensed 2-thioxo-4-thiazolidinone VIII which has been transformed into the acetyl derivative. The thioxo compound VIII may optionally be converted to the methylene compound of formulae I or II as described above. The acetyl group of intermediate IX may be removed upon treatment with aqueous ammonia in a solvent such as acetonitrile to provide compound X. The hydroxy compound X is then converted to the tosyl derivative upon treatment with p-toluenesulfonyl chloride in pyridine, preferably at temperatures of around 0° C. The versatile tosyl intermediate XI may then be transformed into the compounds of formulae I or II upon treatment with an appropriate $HNR^{10}R^{11}$ amine. This latter transformation is best accomplished by allowing XI to react in the presence of a molar excess of the amine. Once again, a solvent such as acetonitrile is useful for accomplishing this transformation.

Those compounds where m is 1 or 2 are readily prepared from the sulfide (m=0) by treatment with an oxidizing agent, such as m-chloroperbenzoic acid, in a suitable solvent for a time sufficient to generate the desired oxidative state.

Depending upon the definitions of $R^1$, $R^2$, and $R^3$, the compounds of formulae I, Ia and II may exist in various isomeric forms. The compounds, formulations and methods of the present invention are not related to any particular isomer but include all possible isomers and racemates.

It will be readily appreciated by one skilled in the art that the aromatic portion of the compounds of the invention (or the compounds employed in the methods of the present invention) can be provided by compounds which are either commercially available or may be readily prepared by known techniques from commercially available starting materials. Similarly, the rhodanine or N-substituted rhodanine starting material is either commercially available or may be prepared by well known methods from commercially available substrates.

The following Examples illustrate the preparation of the compounds of the present invention, as well as compounds which may be employed in the methods of the present invention. The Examples are illustrative only and are not intended to limit the scope of the instant invention in any way.

EXAMPLE 1

5-[(3-methanesulfonamidophenyl)methylene]-2-thioxo-4-thiazolidinone

Thirty seven grams (185.9 mmol) of 3-methanesulfonamidbenzaldehyde, 25.0 g (187.9 mmol) of rhodanine, 48.0 g (585.3 mmol) of anhydrous sodium acetate and 950 ml of acetic acid were stirred while heating at reflux for 20 hours. The reaction was then stirred at room temperature for approximately another 60 hours. The resulting slurry was poured into 3000 ml of a 1:1 ethanol/water mixture. Solids precipitated and were recovered by filtration, washed with water and then vacuum dried to provide 54 g of title compound. m.p. 260°–265° C.

Analysis for $C_{11}H_{10}N_2O_3S_3$ Calculated: C, 42.02; H, 3.20; N 8.91; Found: C, 42.15; H, 3.57; N 8.71.

EXAMPLE 2

5-[(1,3-benzodioxol-5-yl)methylene]-2-thioxo-4-thiazolidinone

Twenty grams (133.2 mmol) of piperonal were reacted with 17.74 g (133.2 mmol)of rhodanine in 38.24 g (466.2 mmol) of glacial acetic acid at reflux for about 3 hours. The mixture was then poured into water and stirred overnight. A precipitate formed which was recovered by filtration and then air dried overnight to provide 27.8 g of title product. m.p. 194°–195° C.

Analysis for $C_{11}H_7N_1O_3S_2$: Calculated: C, 49.80; H, 2.66; N 5.28; S, 24.17; Found: C, 50.04; H, 2.38; N 5.27; S, 23.98.

EXAMPLE 3

5-[(4-quinolinyl)methylene]-2-thioxo-4-thiazolidinone

Rhodanine (2.2 g; 16.5 mmol), 1.3 ml of concentrated ammonium hydroxide and 1 g of ammonium chloride in 20 ml of ethanol were heated on a steam bath for 15 minutes. 4-Quinoline carboxaldehyde (2.6 g; 16.5 mmol) was added and the resulting mixture was heated on the steam bath for another hour. Upon cooling to 5° C. a precipitate formed. This precipitate was recovered by filtration and then washed with water to provide 4 g of title compound, m.p. 325°–328° C.

Analysis for $C_{13}H_8N_2OS_2$: Calculated: C, 57.33; H, 2.96; N 10.29; Found: C, 57.11; H, 3.11; N 10.21.

EXAMPLE 4

5-(diphenylmethylene)-2-thioxo-4-thiazolidinone

One hundred and ninety grams (1.05 mol) of diphenyl kerimine, 140 grams (1.05 mol) of rhodanine, 5 ml of acetic acid and 1500 ml of toluene were heated at reflux for 3 hours. Crystals formed upon cooling. The solvent was decanted, fresh toluene was added to the residue and the resulting suspension was filtered. The recovered crystals were recrystallized from methanol to provide 172.0 g of title product, m.p. 192°–194° C.

Analysis for $C_{16}H_{11}NOS_2$: Calculated: C, 64.62; H, 3.73; O, 5.38; N 4.71; S, 21.56; Found: C, 64.13; H, 3.84; 0, 5.57; N 4.59; S, 22.38.

EXAMPLE 5
5-[(4-phenoxyphenyl)methylene]-2-thioxo-4-thiazolidinone

A mixture of 9.9 g (50.0 mmol) of 4-phenoxybenzaldehyde, 6.8 g (51.1 mmol) of rhodanine, 15.5 g of sodium acetate and 60 ml of acetic acid was heated on a steam bath for two hours. The reaction solution was then poured into water causing crude product to precipitate. The precipitate was filtered and then washed successively with water followed by diethyl ether to provide 8.6 g of title product, m.p. 195°–200° C.

Analysis for $C_{16}H_{11}NO_2S_2$: Calculated: C, 61.32; H, 3.54; N 4.47; Found: C, 61.07; H, 3.63; N 4.47.

The following compounds were synthesized using methods substantially equivalent to those described in Examples 1–5 above or as described elsewhere herein.

EXAMPLE 6
5-(phenylmethylene)-2-thioxo-4-thiazolidinone, m.p. 202°–203.5° C.

EXAMPLE 7
5-[(2-hydroxyphenyl)methylene]-2-thioxo-4-thiazolidinone, m.p. 220°–222° C.

EXAMPLE 8
5-[(4-hydroxyphenyl)methylene]-2-thioxo-4-thiazolidinone, m.p. 287°–290° C.

EXAMPLE 9
5-[(2-nitrophenyl)methylene]-2-thioxo-4-thiazolidinone, m.p. 197.5°–199° C.

EXAMPLE 10
5-[(3-nitrophenyl)methylene]-2-thioxo-4-thiazolidinone, m.p. 277°–280° C.

EXAMPLE 11
5-[(3-hydroxyphenyl)methylene]-2-thioxo-4-thiazolidinone, m.p 242°–244° C.

EXAMPLE 12
5-[(2,4-dimethoxyphenyl)methylene]-2-thioxo-4-thiazolidinone, m.p 253°–255° C.

EXAMPLE 13
5-[(4-fluorophenyl)methylene]-2-thioxo-4-thiazolidlnone, m.p 225°–227° C.

EXAMPLE 14
5-[(2-thienyl)methylene]-2-thioxo-4-thiazolidinone, m.p 231°–233° C.

EXAMPLE 15
5-[(2-furanyl)methylene]-2-thioxo-4-thiazolidinone, m.p 217°–219° C.

EXAMPLE 16
5-[(4-pyridyl)methylene]-2-thioxo-4-thiazolidinone, m.p 297°–298° C.

EXAMPLE 17
5-[(3,4,5-trimethoxyphenyl)methylene]-2-thioxo-4-thiazolidinone, m.p. 203°–205° C.

EXAMPLE 18
5-[(4-methoxyphenyl)methylene]-2-thioxo-4-thiazolidinone, m.p. 252°–254° C.

EXAMPLE 19
5-[(3,4,5-trimethoxyphenyl)methylmethylene]-2-thioxo-4-thiazolidinone, m.p. 210°–213° C.

EXAMPLE 20
5-[(3-methoxy-4-hydroxyphenyl)methylene]-2-thioxo-4-thiazolidinone, m.p. 229°–231° C.

EXAMPLE 21
5-[(4-methoxyphenyl)phenylmethylene]-2-thioxo-4-thiazolidinone, m.p. 169°–171° C.

EXAMPLE 22
5-[(3-pyridyl)methylene]-2-thioxo-4-thiazolidinone, m.p. ~286° C.

EXAMPLE 23
5-[(3-chlorophenyl)methylene]-2-thioxo-4-thiazolidinone, m.p. 233°–235° C.

EXAMPLE 24
5-[(2,3-dimethoxyphenyl)methylene]-2-thioxo-4-thiazolidinone

EXAMPLE 25
5-[(3-methoxyphenyl)methylene]-2-thioxo-4-thiazolidinone

EXAMPLE 26
5-[(2-methoxyphenyl)methylene]-2-thioxo-4-thiazolidinone

EXAMPLE 27
5-[(3-methyl-4-methoxyphenyl)methylene]-2-thioxo-4-thiazolidinone

EXAMPLE 28
5-[[3,5-bis(1,1-dimethylethyl)-4-hydroxyphenyl]methylene]-2-thioxo-4-thiazolidinone, m.p. ~260° C.

EXAMPLE 29
5-[[(1,1'-biphenyl)-2-yl]methylene]-2-thioxo-4-thiazolidinone

EXAMPLE 30
5-[(3-methoxy-4-hydroxyphenyl)methylene]-3-(2-propenyl)-2-thioxo-4-thiazolidinone, m.p. 146°–148° C.

EXAMPLE 31
5-[(3-methoxy-4-heptoxyphenyl)methylene]-2-thioxo-4-thiazolidinone, m.p. 130°–132° C.

EXAMPLE 32
5-[(3-ethoxy-4-hydroxyphenyl)methylene]-2-thioxo-4-thiazolidinone, m.p. 217°–217.5° C.

EXAMPLE 33
5-[(3-methylphenyl)methylene]-2-thioxo-4-thiazolidinone, m.p. 197°–202° C.

EXAMPLE 34
5-[(4-methylphenyl)methylene]-2-thioxo-4-thiazolidinone, m.p. 229°–234° C.

EXAMPLE 35
5-[(2-naphthalenyl)methylene)-2-thioxo-4-thiazolidinone, m.p. 224°–225° C.

EXAMPLE 36
5-[(3,4-dichlorophenyl)methylene]-2-thioxo-4-thiazolidinone

EXAMPLE 37
4-[(2-thioxo-4-thiazolidinone)methylene]benzoic acid, m.p. ~320° C.

EXAMPLE 38
5-[(3,4-diethoxyphenyl)methylene]-2-thioxo-4-thiazolidinone

EXAMPLE 39
5-[(1H-indol-3-yl)methylene]-2-thioxo-4-thiazolidinone

EXAMPLE 40
5-[(3-hydroxy-4-methoxyphenyl)methylene]-2-thioxo-4-thiazolidinone, m.p. 218°–220° C.

EXAMPLE 41

5-[(3-methoxy-4-butoxyphenyl)methylene]-2-thioxo-4-thiazolidinone, m.p. 175°–176° C.

EXAMPLE 42

5-[[(1,1'-biphenyl)-4-yl]methylene]-2-thioxo-4-thiazolidinone, m.p. 245°–250° C.

EXAMPLE 43

5-[(3-hydroxy-4-nitrophenyl)methylene]-2-thioxo-4-thiazolidinone, m.p. ~224° C.

EXAMPLE 44

5-[(3-hydroxyphenyl)methylmethylene]-2-thioxo-4-thiazolidinone

EXAMPLE 45

5-[(3-methoxy-4-pentoxyphenyl)methylene]-2-thioxo-4-thiazolidinone, m.p. 170°–171° C.

EXAMPLE 46

5-[(3-hydroxy-4-ethoxyphenyl)methylene]-2-thioxo-4-thiazolidinone, m.p. >225° C.

EXAMPLE 47

5-[(4-pentoxyphenyl)methylene]-2-thioxo-4-thiazolidinone, m.p. 158.5°–160° C.

EXAMPLE 48

5-[(3-methoxy-4-ethoxyphenyl)methylene]-2-thioxo-4-thiazolidinone, m.p. 207°–207.5° C.

EXAMPLE 49

5-[(3-ethoxy-4-propoxyphenyl)methylene]-2-thioxo-4-thiazolidinone, m.p. 156°–157° C.

EXAMPLE 50

5-[(3-propoxy-4-ethoxyphenyl)methylene]-2-thioxo-4-thiazolidinone, m.p. 186.5°–188° C.

EXAMPLE 51

5-[(3,4-dipropoxyphenyl)methylene]-2-thioxo-4-thiazolidinone, m.p. 167.5°–168.5° C.

EXAMPLE 52

5-[(3-methoxy-4-butoxyphenyl)methylene]-2-thioxo-4-thiazolidinone, sodium salt m.p.>225° C.

EXAMPLE 53

5-[[3,5-bis(1,1-dimethylethyl)-4-hydroxyphenyl]methylene]-4-oxo-2-thioxo-3-thiazolidine acetic acid, m.p. ~265° C.

EXAMPLE 54

5-[(3-methoxy-4-butoxyphenyl)methyl]-2-thioxo-4-thiazolidinone, m.p. 152°–153.5° C.

EXAMPLE 55

5-[(3,5-dichloro-4-hydroxyphenyl)methylene]-2-thioxo-4-thiazolidinone, m.p.>260° C.

EXAMPLE 56

5-[(3-ethoxy-4-butoxyphenyl)methylene]-2-thioxo-4-thiazolidinone

EXAMPLE 57

5-[(3-methoxy-4-pentoxyphenyl)methylene]-2-thioxo-4-thiazolidinone sodium salt, m.p. ~254° C.

EXAMPLE 58

5-[(3-ethoxy-4-methoxyphenyl)methylene]-2-thioxo-4-thiazolidinone, m.p.>225° C.

EXAMPLE 59

5-[[3,5-bis(1-methylpropyl)-4-hydroxyphenyl]methylene]-4-oxo-2-thioxo-3-thiazolidine acetic acid, m.p. 191°–193° C.

EXAMPLE 60

5-[(3,4-dimethoxyphenyl)methylene]-2-thioxo-4-thiazolidinone, m.p. 231.5°–233° C.

EXAMPLE 61

5-[(4-propoxyphenyl)methylene]-2-thioxo-4-thiazolidinone, m.p. 180° C.

EXAMPLE 62

5-[(3,5-dimethyl-4-hydroxyphenyl)methylene]-2-thioxo-4-thiazolidinone, m.p. 260° C.

EXAMPLE 63

5-[(3,5-dimethoxy-4-hydroxyphenyl)methylene]-2-thioxo-4-thiazolidinone, m.p. 230° C.

EXAMPLE 64

5-[(3-methoxy-4-pentoxyphenyl)methyl]-2-thioxo-4-thiazolidinone, m.p. 163°–164° C.

EXAMPLE 65

5-[(3-methoxy-4-pentoxyphenyl)methylene]-2-thioxo-3-methyl-4-thiazolidinone, m.p. 117°–118° C.

EXAMPLE 66

5-[(3-methoxy-4-pentoxyphenyl)methylene]-4-thiazolidinone, m.p. 174°–175° C.

EXAMPLE 67

5-[(3-methoxy-4-pentoxyphenyl)methyl]-4-thiazolidinone, m.p. 108°–109° C.

EXAMPLE 68

5-[(3-methoxy-4-hexoxyphenyl)methylene]-2-thioxo-4-thiazolidinone

EXAMPLE 69

5-[(3-methoxy-4-octoxyphenyl)methylene]-2-thioxo-4-thiazolidinone, m.p. 125°–127° C.

EXAMPLE 70

5-[(3,5-dimethoxy-4-pentoxyphenyl)methylene]-2-thioxo-4-thiazolidinone, m.p. 166°–167° C.

EXAMPLE 71

5-[[3-(1,1-dimethylethyl)-4-hydroxy-5-(methylthiophenyl)phenyl]methylene]-2-thioxo-4-thiazolidinone, m.p. 181°–184° C.

EXAMPLE 72

5-[[3-ethoxy-4-hydroxy-5-(methylthiophenyl)phenyl]methylene]-2-thioxo-4-thiazolidinone, m.p. 190°–192° C.

EXAMPLE 73

5-[[3-ethoxy-4-hydroxy-5-(methylthiophenyl)phenyl]methylene]-2-thioxo-3-methyl-4-thiazolidinone, m.p. 137° C.

EXAMPLE 74

5-[[3-ethoxy-4-hydroxy-5-(methylthiophenyl)
phenyl]methylene]-4-oxo-2-thioxo-3-thiazolidine
acetic acid m.p. 202°–206° C.

EXAMPLE 75
5-[(1-naphthyl)methylene]-2-thioxo-4-
thiazolidinone, m.p. 224°–225° C.

EXAMPLE 76
5-[(2-naphthyl)methylmethylene]-2-thioxo-4-
thiazolidinone

EXAMPLE 77
5-[(3-phenoxyphenyl)methylene]-2-thioxo-4-
thiazolidinone

EXAMPLE 78
5-[(3-phenoxyphenyl)methylmethylene]-2-thioxo-4-
thiazolidinone

EXAMPLE 79
5-[[3-(methyloxyphenyl)phenyl]methylene]-2-
thioxo-4-thiazolidinone, m.p. 177°–180° C.

EXAMPLE 80
5-[(3-methoxy-4-heptoxyphenyl)methylene]-2-
thioxo-3-amino-4-thiazolidinone, m.p. 118°–121° C.
(dec).

EXAMPLE 81
5-[(3-methoxy-4-heptoxyphenyl)methylene]-2-
thioxo-3-dimethylamino-4-thiazolidinone Two hundred and fifty milligrams (1 mmol) of
3-methoxy-4-heptoxy benzaldehyde, 233 mg (1.2 mmol) of
2-(N-dimethylamino-dithiocarboxamido)acetic acid (a compound of formula VI, above), 330 mg (4 mmol) of anhydrous sodium acetate and 5 ml of acetic acid were stirred while heating at reflux for 15 hours. The reaction was then quenched by pouring the reaction solution into 10 ml of an ice/water mixture. The resulting solids were recovered by filtration, washed with ethyl acetate and then water to provide 450 mg of impure title compound. The impure compound was purified via recrystallization from hexane/methylene chloride to provide 180 mg of pure title compound. m.p. 105°–108° C.

EXAMPLE 82
5-[[4-(dimethylamino)phenyl]methylene]-2-thioxo-
4-thiazolidinone

EXAMPLE 83
5-[(4-heptoxyphenyl)methylene]-2-thioxo-3-
dimethylamino-4-thiazolidinone, m.p. 80° C.

EXAMPLE 84
5-[(3-ethoxy-4-hydroxyphenyl)methylene]-2-thioxo-
3-cyclohexyl-4-thiazolidinone, m.p. 122°–123° C.

EXAMPLE 85
5-[[3,5-bis(1,1-dimethylethyl)-4-hydroxyphenyl]
methylene]-2-thioxo-3-methyl-4-thiazolidinone,
m.p.>200° C.

EXAMPLE 86
5-[(3-methanesulfonamidophenyl)methylene]-4-oxo-
2-thioxo-3-thiazolidine acetic acid, m.p.>230° C.

EXAMPLE 87
5-[[3,5-bis(1,1-dimethylethyl)-4-methoxyphenyl]
methylene]-2-thioxo-4-thiazolidinone, m.p.
234°–236° C.

EXAMPLE 88
5-[(3-ethoxy-4-hydroxyphenyl)methylene]-2-thioxo-
3-methyl-4-thiazolidinone, m.p. 157° C.

EXAMPLE 89
5-[[3-ethoxy-4-hydroxy-5-(methylthiophenyl)
phenyl]methylene]-2-thioxo-3-dimethylamino-4-
thiazolidinone, m.p. 137°–141° C.

EXAMPLE 90
5-[(3-ethoxy-4-hydroxyphenyl)methylene]-2-thioxo-
3-dimethylamino-4-thiazolidinone, m.p. 194°–198°
C.

EXAMPLE 91
5-[(3,4-dipentoxyphenyl)methylene]-4-oxo-2-
thioxo-3-thiazolidine acetic acid, m.p. 179°–182°
C.

EXAMPLE 92
5-[[3-(1,1-dimethylethyl)-4-hydroxyphenyl]
methylene]-2-thioxo-3-methyl-4-thiazolidinone,
m.p.>230° C.

EXAMPLE 93
5-[(3,4-diheptoxyphenyl)methylene]-2-thioxo-3-
dimethylamino-4-thiazolidinone, m.p. 67° C.

EXAMPLE 94
5-[(3,4-dibutoxyphenyl)methylene]-2-thioxo-3-
dimethylamino-4-thiazolidinone, m.p. 92° C.

EXAMPLE 95
5-[(3-methoxy-4-heptoxyphenyl)methylene]-2-
thioxo-3-(2-propenyl)-4-thiazolidinone, m.p.
75°–78° C.

The present invention provides a method for lowering blood glucose levels in mammals comprising administering a therapeutically effective amount of a compound of formula I. The term "therapeutically effective amount", as defined herein, means the amount of compound necessary to provide a hypoglycemic effect following administration, preferably to a human susceptible to adult onset diabetes.

The hypoglycemic activity of the compounds of the present invention was determined by testing the efficacy of the compounds in vivo in male viable yellow obese-diabetic mice. The test procedure is described in detail below.

Test formulations were prepared by dissolving the test compound in a saline solution containing 2% Emulphor (a polyoxyethylated vegetable oil surfactant from GAF Corp.) to provide the dose level desired. Each test formulation was administered to six viable yellow obese-diabetic mice intraperitoneally at the beginning of the experiment. Blood glucose levels were determined immediately before the first dose and at 2 and 4 hours thereafter using glucose oxidase. A mean was taken of the 6 values obtained before the first dose and at the 2 and 4 hour intervals. The 2 and 4 hour mean values, calculated as a percentage of the first dose mean value, are reported in Table 1, below. In Table 1, Column 1 provides the example number of the test compound, Column 2 provides the dose level of compound tested, and Columns 3 and 4 provide a measurement of the test animal's blood glucose level 2 and 4 hours after test compound administration, respectively, as a percentage of the test animal's pre-administration blood glucose level.

TABLE 1

HYPOGLYCEMIC ACTIVITY OF TEST COMPOUNDS IN OBESE DIABETIC MICE

| Example # of Compound Tested | Dose (mg/kg) | Percent of Initial Blood Glucose Level After 2 hrs. | Percent of Initial Blood Glucose Level After 4 hrs. |
|---|---|---|---|
| 1 | 50 | 82 ± 5 | 75 ± 2 |
| 2 | 50 | 96 ± 1 | 82 ± 3 |
| 3 | 50 | 90 ± 10 | 73 ± 3 |
| 4 | 50 | 91 ± 4 | 72 ± 7 |
| 5 | 50 | 79 ± 4 | 71 ± 3 |
| 6 | 50 | 85 ± 6 | 72 ± 4 |
| 6 | 50 | 92 ± 4 | 79 ± 4 |
| 7 | 50 | 80 ± 4 | 91 ± 7 |
| 8 | 50 | 94 ± 4 | 84 ± 6 |
| 9 | 50 | 91 ± 8 | 83 ± 6 |
| 10 | 50 | 89 ± 4 | 80 ± 4 |
| 11 | 50 | 84 ± 3 | 85 ± 6 |
| 12 | 50 | 90 ± 7 | 69 ± 6 |
| 13 | 50 | 94 ± 4 | 88 ± 5 |
| 14 | 50 | 84 ± 7 | 71 ± 8 |
| 15 | 50 | 73 ± 5 | 62 ± 4 |
| 16 | 50 | 94 ± 8 | 96 ± 9 |
| 17 | 50 | 88 ± 8 | 89 ± 10 |
| 18 | 50 | 89 ± 4 | 88 ± 5 |
| 19 | 50 | 85 ± 14 | 75 ± 4 |
| 20 | 50 | 76 ± 3 | 70 ± 5 |
| 21 | 50 | 99 ± 4 | 81 ± 6 |
| 22 | 50 | 77 ± 5 | 67 ± 2 |
| 22 | 50 | 77 ± 6 | 69 ± 6 |
| 23 | 50 | 74 ± 6 | 90 ± 6 |
| 24 | 50 | 78 ± 4 | 80 ± 5 |
| 25 | 50 | 78 ± 4 | 74 ± 4 |
| 25 | 25 | 84 ± 5 | 87 ± 6 |
| 26 | 50 | 80 ± 4 | 75 ± 2 |
| 27 | 50 | 93 ± 3 | 84 ± 6 |
| 28 | 50 | 83 ± 9 | 79 ± 7 |
| 29 | 50 | 84 ± 5 | 77 ± 6 |
| 30 | 50 | 78 ± 7 | 81 ± 5 |
| 31 | 50 | 76 ± 7 | 76 ± 5 |
| 32 | 50 | 75 ± 4 | 80 ± 8 |
| 32 | 50 | 80 ± 18 | 66 ± 11 |
| 33 | 50 | 91 ± 6 | 86 ± 7 |
| 34 | 50 | 85 ± 8 | 79 ± 9 |
| 35 | 50 | 83 ± 5 | 85 ± 6 |
| 36 | 50 | 81 ± 7 | 90 ± 8 |
| 37 | 50 | 89 ± 4 | 80 ± 4 |
| 38 | 50 | 60 ± 5 | 59 ± 4 |
| 38 | 50 | 96 ± 6 | 80 ± 3 |
| 38 | 50 | 86 ± 4 | 81 ± 5 |
| 38 | 25 | 69 ± 9 | 65 ± 7 |
| 38 | 10 | 72 ± 4 | 71 + 6 |
| 38 | 10 | 73 ± 8 | 59 ± 7 |
| 39 | 50 | 83 ± 4 | 76 ± 4 |
| 40 | 50 | 78 ± 5 | 72 ± 4 |
| 41 | 50 | 61 ± 3 | 51 ± 4 |
| 41 | 50 | 64 ± 6 | 54 ± 5 |
| 41 | 50 | 77 ± 5 | 62 ± 5 |
| 41 | 50 | 77 ± 5 | 72 ± 8 |
| 41 | 25 | 58 ± 6 | 45 ± 5 |
| 41 | 25 | 72 ± 7 | 64 ± 4 |
| 41 | 25 | 74 ± 7 | 70 ± 8 |
| 41 | 25 | 87 ± 5 | 85 ± 6 |
| 41 | 10 | 80 ± 7 | 59 ± 4 |
| 41 | 10 | 97 ± 7 | 75 ± 5 |
| 41 | 10 | 92 ± 7 | 92 ± 7 |
| 41 | 5 | 93 ± 10 | 71 ± 4 |
| 41 | 5 | 95 ± 4 | 97 ± 5 |
| 42 | 50 | 87 ± 8 | 70 ± 8 |
| 43 | 50 | 92 ± 7 | 88 ± 4 |
| 44 | 50 | 98 ± 4 | 88 ± 5 |
| 45 | 50 | 76 ± 7 | 57 ± 3 |
| 45 | 50 | 68 ± 2 | 66 ± 4 |
| 45 | 25 | 93 ± 4 | 87 ± 5 |
| 45 | 25 | 83 ± 10 | 78 ± 12 |
| 46 | 50 | 79 ± 4 | 77 ± 5 |
| 47 | 50 | 99 ± 14 | 76 ± 8 |
| 48 | 50 | 70 ± 3 | 65 ± 3 |
| 48 | 25 | 87 ± 4 | 81 ± 5 |
| 49 | 50 | 83 ± 5 | 77 ± 7 |
| 50 | 50 | 75 ± 5 | 69 ± 5 |
| 51 | 50 | 89 ± 7 | 85 ± 8 |
| 52 | 50 | 73 ± 3 | 61 ± 4 |
| 53 | 100 | 83 ± 9 | 80 ± 14 |
| 53 | 50 | 73 ± 4 | 55 ± 5 |
| 54 | 50 | 76 ± 7 | 74 ± 6 |
| 55 | 50 | 81 ± 3 | 75 ± 3 |
| 56 | 50 | 78 ± 4 | 72 ± 3 |
| 56 | 25 | 81 ± 8 | 75 ± 3 |
| 56 | 10 | 94 ± 4 | 97 ± 4 |
| 57 | 50 | 63 ± 6 | 58 ± 7 |
| 57 | 50 | 69 ± 5 | 63 ± 7 |
| 57 | 25 | 67 ± 7 | 66 ± 7 |
| 57 | 25 | 79 ± 10 | 70 ± 4 |
| 57 | 10 | 95 ± 3 | 87 ± 6 |
| 57 | 5 | 82 ± 6 | 68 ± 5 |
| 58 | 50 | 67 ± 2 | 75 ± 5 |
| 59 | 50 | 62 ± 5 | 59 ± 9 |
| 60 | 50 | 85 ± 4 | 78 ± 3 |
| 60 | 50 | 102 ± 6 | 81 ± 5 |
| 60 | 25 | 87 ± 7 | 89 ± 6 |
| 61 | 50 | 76 ± 5 | 61 ± 5 |
| 61 | 50 | 98 ± 8 | 79 ± 4 |

The hypoglycemic activity of the compounds of the present invention was confirmed in a second in vivo test system; namely, the normal fed rat system. The procedure used in this test system is described below.

Male Sprague Dawley rats (Charles River Laboratories) weighing 175–200 g were used in this test system. Test formulations were prepared by suspending the test compound in 5% acacia (concentration of the drug was adjusted such that 0.25 ml/100 g body weight administered orally gave the desired dose on a body weight basis). The desired dose level of each test formulation was administered to four rats by oral gavage at the beginning of the experiment. Blood glucose levels were determined immediately before the first dose and at 3 and 5 hours thereafter by an enzymatic procedure employing glucose oxidase and peroxidase coupled with a chromogenic oxygen acceptor. A mean was taken of the 4 values obtained before the first dose and at the 3 and 5 hour intervals. The 3 and 5 hour mean values, calculated as a percentage of the first dose mean value, are reported in Table 2, below. In Table 2, Column 1 provides the example number of the test compound, Column 2 provides the dose level of compound tested, and Columns 3 and 4 provide a measurement of the test animal's blood glucose level 3 and 5 hours after test compound administration, respectively, as a percentage of the test animal's pre-administration blood glucose level.

TABLE 2

HYPOGLYCEMIC ACTIVITY OF TEST COMPOUNDS IN NORMAL FED RATS

| Example # of Compound Tested | Dose (mg/kg) | Percent of Initial Blood Glucose Level | |
|---|---|---|---|
| | | After 3 hrs. | After 5 hrs. |
| 15 | 167 | 84 | 87 |
| 16 | 200 | 92 | 79 |
| 17 | 200 | 78 | 68 |
| 22 | 200 | 84 | 68 |
| 24 | 200 | 100 | 100 |
| 25 | 200 | 100 | 100 |
| 26 | 200 | 100 | 100 |
| 31 | 200 | 95 | 92 |
| 32 | 200 | 100 | 96 |
| 38 | 200 | 90 | 74 |
| 41 | 160 | 76 | 67 |
| 45 | 167 | 61 | 63 |
| 47 | 200 | 82 | 73 |
| 48 | 167 | 87 | 81 |
| 49 | 200 | 100 | 98 |
| 56 | 150 | 79 | 65 |
| 57 | 200 | 84 | 73 |
| 58 | 200 | 100 | 100 |
| 61 | 200 | 89 | 82 |
| 62 | 200 | 78 | 53 |
| 63 | 200 | 69 | 52 |
| 64 | 200 | 91 | 89 |
| 65 | 200 | 100 | 91 |
| 66 | 200 | 100 | 86 |
| 67 | 200 | 92 | 88 |
| 68 | 200 | 88 | 89 |
| 69 | 200 | 93 | 88 |

The hypoglycemic activity of the compounds of the present invention was confirmed in yet a third in vivo test system; namely, the obese diabetic Zucker rat (Zucker Diabetic Fatty Rat) test system. The rats used in this test system were 6 to 8 months old, weighed between 550 to 625 grams and had a pre-drug blood glucose level between 250 to 350 mg/dl. The procedure used in this test system is the same as that described for the normal fed rat test system, above. The results of such tests are set forth in Table 3, below. The format of Table 3 is the same as that used in Table 2.

TABLE 3

HYPOGLYCEMIC ACTIVITY OF TEST COMPOUNDS IN OBESE DIABETIC ZUCKER RATS

| Example # of Compound Tested | Dose (mg/kg) | Percent of Initial Blood Glucose Level | |
|---|---|---|---|
| | | After 3 hrs. | After 5 hrs. |
| 22 | 50 | 53 | 56 |
| 45 | 167 | 30 | 20 |
| 47 | 167 | 74 | 66 |
| 56 | 50 | 79 | 66 |

Finally, the long-term hypoglycemic activity of the compounds of the present invention was tested in yet another in vivo test system. This long-term test system entailed incorporating test compound into the test animal's diet at various concentrations (control animal's diet contained no test compound). Such diet was then fed to the test or control animals for either 14 or 21 days. Each test or control animal was then bled from the tail (200–400 µl sample of blood) at 0 (before diet started), 7, 14 and, if appropriate, 21 and 28 days after diet administration was started. Plasma samples were then obtained from each blood sample collected and the glucose concentration of such plasma samples was determined enzymatically.

The results of the long-term hypoglycemic test system described above are set forth in Table 4, below. In Table 4, Column 1 describes the type of rodent used in the test system, Column 2 provides the example number of the test compound or indicates that the numbers reported are for a control animal, Column 3 provides the concentration, in percent, of test compound in the test or control animal's diet. Columns 4–8 provide the plasma glucose concentration at days 0, 7, 14 and, if appropriate, 21 and 28, respectively, for the animals tested. Glucose lowering was not associated with depressed diet consumption.

TABLE 4

LONG-TERM HYPOGLYCEMIC ACTIVITY OF TEST COMPOUNDS

| Type of Rodent* | Example No. of Cmpd. Tested | Concentration of Test Cmpd. in Diet (%) | Plasma Glucose Concentration (mg/dl) | | | | |
|---|---|---|---|---|---|---|---|
| | | | 0 | 7 | 14 | 21 | 28 |
| ZDF | 45 | 0.1 | 388 | 140 | 155 | — | — |
| ZDF | control | — | 416 | 364 | 445 | — | — |
| ZDF | 45 | 0.1 | 464 | 215 | 238 | 285 | — |
| ZDF | 45 | 0.025 | 467 | 451 | 452 | 517 | — |
| ZDF | control | — | 478 | 499 | 571 | 565 | — |
| ZDF | 45 | 0.1 | 357 | 171 | 166 | — | — |
| ZDF | 64 | 0.1 | 339 | 187 | 182 | — | — |
| ZDF | control | — | 343 | 423 | 454 | — | — |
| ZDF | 45 | 0.1 | 309 | 137 | 142 | — | — |
| ZDF | 71 | 0.1 | 311 | 237 | 232 | — | — |
| ZDF | 70 | 0.1 | 300 | 190 | 195 | — | — |
| ZDF | control | — | 317 | 286 | 255 | — | — |
| Male A$^{vy}$/a (Harlan) | 45 | 0.1 | 438 | 338 | 315 | 287 | 295 |
| Male A$^{vy}$/a (Harlan) | 38 | 0.1 | 340 | 351 | 328 | 303 | 331 |
| Male A$^{vy}$/a | control | — | 429 | 414 | 410 | 390 | 359 |

TABLE 4-continued

LONG-TERM HYPOGLYCEMIC ACTIVITY OF TEST COMPOUNDS

| Type of Rodent* | Example No. of Cmpd. Tested | Concentration of Test Cmpd. in Diet (%) | Plasma Glucose Concentration (mg/dl) | | | | |
|---|---|---|---|---|---|---|---|
| | | | 0 | 7 | 14 | 21 | 28 |
| (Harlan) | | | | | | | |

*ZDF = 8 week old male Zucker Diabetic Fatty rat; $A^{vy/a}$ = viable yellow mouse The present invention also provides a method for treating Alzheimer's disease in mammals comprising administering a therapeutically effective amount of a compound of formula Ia. The term "therapeutically effective amount", as defined for this method, means the amount of compound necessary to reduce, eliminate or prevent the physiological effects or causes of Alzheimer's disease following administration, preferably to a human suffering from or susceptible to Alzheimer's disease.

Alzheimer's disease is a degenerative disorder of the human brain. Clinically, it appears as a progressive dementia. Its histopathology is characterized by degeneration of neurons, gliosis, and the abnormal deposition of proteins in the brain. Proteinaceous deposits (called "amyloid") appear as neurofibrillary tangles, amyloid plaque cores, and amyloid of the congophilic angiopathy. [For reviews, see, *Alzheimer's Disease*, (B. Reisberg, ed., The Free Press 1983).]

While there is no general agreement as to the chemical nature of neurofibrillary tangles, the major constituent of both the amyloid plaque cores and the amyloid of the congophilic angiopathy has been shown to be a 4500 Dalton protein originally termed β-protein or amyloid A4. Throughout this document this protein is referred to as β-amyloid peptide or protein.

β-amyloid peptide is proteolytically derived from a transmembrane protein, the amyloid precursor protein (APP). Different splice forms of the amyloid precursor protein are encoded by a widely expressed gene. see, e.g., K. Beyreuther and B. Müller-Hill, *Annual Reviews in Biochemistry*, 58:287–307 (1989). β-amyloid peptide consists, in its longest forms, of 42 or 43 amino acid residues. J. Kang, et al., *Nature (London)*, 325:733–736 (1987). These peptides, however, vary as to their amino-termini. C. Hilbich, et al., *Journal of Molecular Biology*, 218:149–163 (1991).

Because senile plaques are invariably surrounded by dystrophic neurites, it was proposed early that β-amyloid peptide is involved in the loss of neuronal cells that occurs in Alzheimer's disease. B. Yankner and co-workers were the first to demonstrate that synthetic β-amyloid peptide could be neurotoxic in vitro and in vivo. B. A. Yankner, et al., *Science*, 245:417 (1989); see also, N. W. Kowall, et al., *Proceedings of the National Academy of Sciences, U.S.A.*, 88:7247 (1991). Other research groups, however, were unable to consistently demonstrate direct toxicity with β-amyloid peptide. see, e.g., *Neurobiology of Aging*, 13:535 (K. Kosik and P. Coleman, eds. 1992). Even groups receiving β-amyloid peptide from a common source demonstrate conflicting results. D. Price, et al., *Neurobiology of Aging*, 13:623–625 (1991) (and the references cited therein).

As mentioned supra, cells have alternative mechanisms for processing APP which can result in the formation of the β-amyloid protein and subsequently, the senile plaques. It is likely that this alternative processing route occurs in the lysosomes. It has been found that compounds that inhibit lysosomal enzymes inhibit the fragment formation. see, e.g., *Science*, 155:689 (1992).

A lysosome is a membranous reservoir of hydrolyric enzymes responsible for the intracellular digestion of macromolecules. Lysosomes are known to contain approximately forty hydrolyric enzymes, including proteases, nucleases, glycosidases, lipases, phospholipases, phosphatases and sulfatases. These enzymese are all acid hydrolases which are optimally active at about pH 5. Therefore, it is necessary to determine which enzyme or enzymes are responsible for this alternative processing of the APP and the consequent formation of the β-amyloid protein.

Abnormally high concentrations of the proteases cathepsins D and B have been observed in the brains of patients with early-onset Alzheimer's disease. Yu Nakamura, et al., *Neuroscience Letters*, 130, 195–198 (1991). Furthermore, elevated activity for cathepsin D has been observed in the brains of Alzheimer's patients. M. Takeda, et al., *Neurochemistry Research*, (abstract), 11:117 (1986). Cathepsin D is a lysosomal endoprotease that is present in all mammalian cells. see, e.g., "Proteinases in Mammalian Cells and Tissues," ed. (A. J. Barret, ed. 1977) pp. 209–248. It is the only aspartyl protease that is known to be a lysosomal enzyme.

The cathepsins are a family of hydrolase enzymes that are usually located in the lysosomes. These enzymes are endopeptidases with an acidic optimum pH. Cathepsin A is a serine carboxypeptidase, cathepsin C [EC 3.4.14.1] is a dipeptidyl peptidase, cathepsin D [EC 3.4.23.5] is an aspartyl protease, and cathepsin $B_2$ [EC 3.4.16.1] is a serine carboxypeptidase. Cathepsin B [EC 3.4.22.1] (also known as cathepsin $B_1$) and cathepsin L [EC 3.4.22.15] are thiol proteases having activity within the lysosomes.

It has been found that inhibition of cathepsin D using an aspartyl protease inhibitor reduces the formation of β-amyloid protein and the resultant senile plaque. As such, compounds which inhibit cathepsins (and, in particular, cathepsin D) or reduce the formation of β-amyloid protein would be expected to be useful in treating Alzheimer's disease. Such activities were demonstrated in the following test systems.

CATHEPSIN D PERCENT INHIBITION ACTIVITY

A fluorometric assay was adapted from the method disclosed by Murakami et al., *Anal. Biochem.* 110:232–239

(1981) for measuring renin activity. Human liver cathepsin D (Athens Research and Technology, Athens, Ga.) was diluted in assay buffer, 200 mM NaOAc, pH 4.5, 150 mM NaCl to 500 ng/mL and then 100 µL of this cathepsin D solution was added to each well of a 96 well plate with the exception of control wells which received just 100 µL of assay buffer. Compound stocks were prepared by dissolving a sufficient quantity of the particular compound to be tested in DMSO such that various concentrations (either 10 µg/ml, 8.3 µg/ml or 4.15 µg/ml) of test compound in DMSO were obtained and then 5 µL of the compound stock was added to each of the wells prepared above. Blank and enzyme control wells each received 5 µL of the DMSO vehicle.

Following a ten minute incubation at 25° C. to allow enzyme/compound interaction, 5 µL of a 500 µM solution of a derivative of a known porcine renin tetradecapeptide fluorometric substrate (Bachem Biosciences, Inc. 1993 Catalog ID No. I-1340; Bachem Biosciences, Philadelphia, Pa.) in DMSO was added per well to initiate the reaction. After incubation at 37° C. for 30 minutes, cathepsin D activity was terminated by the addition of 100 µL per well of 400 mU/mL microsomal leucine aminopeptidase (EC 3.4.11.2, Sigma, St. Louis, Mo.) in 1M Tris-HCl, pH 8.0.

The plates were then analyzed in a fluorometer (CytoFluor 2350, Millipore, Bedford, Mass.) with an excitation wavelength of 360 nm and an emission wavelength of 460 nm, in order to check for background fluorescence due to test compounds. Following a two hour incubation at 37° C., to allow the aminopeptidase to release the fluorophore, 7-amido-4-methylcoumarin (AMC) from the products of cathepsin D cleavage, the plates were again analyzed in the fluorometer. In order to check for potential false positives, i.e., inhibitors of microsomal leucine aminopeptidase, residual aminopeptidase activity was monitored directly in each well by the addition of 20 µL/well of 2.5 mM Leu-pNA (Bachem Biosciences, Philadelphia, Pa.) in 10% DMSO. Aminopeptidase activity was measured as an increase in the absorbance of 405 nm in a $UV_{max}$ microplate reader (Molecular Devices, Menlo Park, Calif.).

Cathepsin D activity was linear under these conditions and the results are expressed as a percentage of the controls in Table 5, below. All results presented are the mean and standard deviation of at least four replicate assays.

TABLE 5

CATHEPSIN D INHIBITION ACTIVITY

| Example No. | Compound Stock Concentration (µg/ml) | % Inhibition of Cathepsin D |
|---|---|---|
| 1 | 10.0 | 36 |
| 4 | 10.0 | 50 |
| 5 | 10.0 | 76 |
| 5 | 8.3 | 100 |
| 6 | 10.0 | 29 |
| 8 | 10.0 | 64 |
| 18 | 10.0 | 38 |
| 21 | 4.15 | 40 |
| 31 | 10.0 | 88.5 |
| 31 | 4.15 | 69.5 |
| 32 | 4.15 | 75 |
| 35 | 4.15 | 57 |
| 42 | 10.0 | 87.5 |

TABLE 5-continued

CATHEPSIN D INHIBITION ACTIVITY

| Example No. | Compound Stock Concentration (µg/ml) | % Inhibition of Cathepsin D |
|---|---|---|
| 42 | 4.15 | 78 |
| 45 | 8.3 | 95 |
| 45 | 4.15 | 49.5 |
| 47 | 4.15 | 60.5 |
| 50 | 4.15 | 40 |
| 55 | 4.15 | 90 |
| 56 | 4.15 | 73 |
| 60 | 8.3 | 38 |
| 60 | 4.15 | 45.5 |
| 63 | 4.15 | 53 |
| 68 | 4.15 | 53.7 |
| 69 | 4.15 | 51 |
| 70 | 4.15 | 66 |
| 71 | 10.0 | 76 |
| 71 | 8.3 | 94 |
| 72 | 8.3 | 96 |
| 72 | 4.15 | 88 |
| 73 | 8.3 | 76 |
| 73 | 4.15 | 69 |
| 74 | 8.3 | 95 |
| 75 | 10.0 | 43 |
| 76 | 10.0 | 32 |
| 77 | 10.0 | 87 |
| 77 | 4.15 | 64 |
| 78 | 4.15 | 41 |
| 79 | 4.15 | 87 |
| 80 | 8.3 | 33 |
| 81 | 8.3 | 21 |
| 82 | 10.0 | 73.5 |
| 83 | 4.15 | 47 |
| 34 | 4.15 | 51 |
| 86 | 8.3 | 42 |
| 88 | 8.3 | 82 |
| 88 | 4.15 | 67 |
| 89 | 8.3 | 71 |
| 90 | 8.3 | 92 |
| 90 | 4.15 | 79 |
| 91 | 4.15 | 72 |
| 92 | 4.15 | 74 |
| 94 | 4.15 | 48 |
| 95 | 8.3 | 36 |

CATHEPSIN D INHIBITION $IC_{50}$ ACTIVITY

The above assay was repeated with the exception that the compound stocks were prepared in concentrations such that $IC_{50}$ values (concentration of test compound at which 50% inhibition of cathepsin D was obtained) for the test compounds could be determined. The results obtained from such assay system are set forth in Table 6 below.

TABLE 6

| Example No. | $IC_{50}$ (µM) |
|---|---|
| 5 | 3.6 |
| 28 | 3.1 |
| 31 | 1.9 |
| 35 | 8.9 |
| 42 | 1.7 |
| 47 | 5.2 |
| 56 | 12.3 |
| 60 | 14.75 |
| 68 | 10.2 |
| 69 | 2.1 |
| 70 | 5.4 |
| 71 | 2.1 |
| 72 | 1.7 |

TABLE 6-continued

| Example No. | IC$_{50}$ (µM) |
|---|---|
| 73 | 9.9 |
| 74 | 5.8 |
| 77 | 3.7 |
| 78 | 22.1 |
| 79 | 3.7 |
| 80 | 47.0 |
| 81 | 319.4 |
| 85 | 14.3 |
| 87 | 2.2 |
| 88 | 11.2 |
| 89 | 9.2 |
| 90 | 7.7 |
| 91 | 9.7 |
| 92 | 3.9 |
| 93 | 7.5 |

β-AMYLOID PROTEIN PRODUCTION INHIBITION

Two cell lines (human kidney cell line 293 and Chinese hamster ovary cell line CHO) were stably transfected with the gene for APP751 containing the double mutation Lys-651-Met-652 to Asn-651-Leu-652 (APP-751 numbering) commonly called the Swedish mutation using the method described in Citron et al., Nature 360:672–674 (1992). The transfected cell lines were designated as 293 751 SWE and CHO 751 SWE, and were plated in Corning 96 well plates at 2.5×10$^4$ or 1×10$^4$ cells per well respectively in Dulbecco's minimal essential media (DMEM) plus 10% fetal bovine serum. Following overnight incubation at 37° C. in an incubator equilibrated with 10% carbon dioxide ($CO_2$), the media were removed and replaced with 200 µL per well of conditioned media (media containing compound stocks; compound stocks diluted with media such that the concentration of DMSO in the media/compound stock solution did not exceed 0.5%) for a two hour pretreatment period during which the cells were incubated as described above. These compound stocks were prepared by dissolving a sufficient quantity of the particular compound to be tested in DMSO such that various concentrations were obtained. After this pretreatment period, the conditioned media was removed and replaced with fresh conditioned media and the cells were incubated for an additional two hours.

After treatment, plates were centrifuged in a Beckman GPR at 1200 rpm for five minutes at room temperature to pellet cellular debris from the conditioned media. From each well, 100 µL of conditioned media were transferred into an ELISA plate precoated with antibody 266 [Seubert et al., Nature, 359:325–327 (1992)] and stored at 4° C. overnight prior to the completion of the ELISA assay the next day.

Cytotoxic effects of the compounds were measured by a modification of the method of Hansen et al., J. Immun. Meth. 119:203–210 (1989). To the cells remaining in the tissue culture plate, was added 25 µL of a 3-(4,5-dimethylthiazol-2-yl)-2,5-diphenyltetrazolium bromide (MTT) stock solution (5 mg/mL) to a final concentration of 1 mg/mL. Cells vere incubated at 37° C. for one hour, and cellular activity was stopped by the addition of an equal volume of MTT lysis buffer (20% w/v sodium dodecylsulfate in 50% DMF, pH 4.7). Complete extraction was achieved by overnight shaking at room temperature. The difference in the OD$_{562\,nm}$ and the OD$_{650\,nm}$ was measured in a Molecular Devices UV$_{max}$ microplate reader as an indicator of the cellular viability.

The results of the β-amyloid protein ELISA were fit to a standard curve and expressed as ng/mL β-amyloid protein peptide. In order to normalize for cytotoxicity, these β-amyloid protein results were divided by the cytotoxicity results and expressed as a percentage of the results from a drug-free control.

TABLE 7

β-AMYLOID PROTEIN INHIBITION

| Example No. | Compound Stock Concentration (µg/ml) | % Inhibition of β-Amyloid Protein |
|---|---|---|
| 5 | 10.0 | 47 |
| 31 | 10.0 | 57 |
| 31 | 5.0 | 37 |
| 31 | 2.5 | 28 |
| 31 | 1.25 | 15 |
| 31 | 0.62 | 7 |
| 31 | 0.31 | 0 |
| 42 | 10.0 | 51 |
| 42 | 5.0 | 35 |
| 42 | 2.5 | 16 |
| 42 | 1.25 | 14 |
| 42 | 0.62 | 11 |
| 42 | 0.31 | 8 |
| 70 | 10.0 | 38 |
| 71 | 10.0 | 65 |
| 77 | 10.0 | 25 |
| 81 | 10.0 | 100 |

As can be seen from the data in Tables 5, 6 and 7, the compounds of formula Ia can be administered for prophylactic and/or therapeutic treatment of diseases related to the deposition of β-amyloid protein such as Alzheimer's disease, Down's syndrome, and advanced aging of the brain. In therapeutic applications, the compounds are administered to a host already suffering from the disease. The compounds will be administered in an amount sufficient to inhibit further deposition of β-amyloid protein plaque.

For prophylactic applications, the compounds of formula Ia are administered to a host susceptible to Alzheimer's disease or a β-amyloid protein related disease, but not already suffering from such disease. Such hosts may be identified by genetic screening and clinical analysis, as described in the medical literature. see e.g., Goate, Nature 349:704–706 (1991). The compounds will be able to inhibit or prevent the formation of the β-amyloid protein plaque at a symptomatically early stage, preferably preventing even the initial stages of the β-amyloid protein disease.

The compounds of the present invention and the compounds utilized in the methods of the present invention are effective over a wide dosage range. For example, dosages per day will normally fall within the range of about 0.5 to about 500 mg/kg of body weight. In the treatment of adult humans, the range of about 1.0 to about 100 mg/kg, in single or divided doses, is preferred. However, it will be understood that the amount of the compound actually administered will be determined by a physician in light of the relevant circumstances including the condition to be treated, the choice of compound to be administered, the age, weight, and response of the individual patient, the severity of the patient's symptoms and the chosen route of administration. Therefore, the above dosage ranges are not intended to limit the scope of the invention in any way. While the present compounds are preferably administered orally, the compounds may also be administered by a variety of other routes such as the transdermal, subcutaneous, intranasal, intramuscular and intravenous routes.

While it is possible to administer a compound of the invention, or a compound used in the methods of this invention, directly, the compounds are preferably employed in the form of a pharmaceutical formulation comprising a pharmaceutically acceptable carrier, diluent or excipient and a compound of the invention. Such formulations will contain from about 0.01 percent to about 90 percent of a compound of the invention.

In making the formulations of the present invention, the active ingredient will usually be mixed with at least one carrier, or diluted by at least one carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the formulations can be in the form of tablets, granules, pills, powders, lozenges, sachets, cachets, elixirs, emulsions, solutions, syrups, suspensions, aerosols (as a solid or in a liquid medium) and soft and hard gelatin capsules.

Examples of suitable carriers, diluents and excipients include lactose, dextrose, sucrose, sorbitol, mannitol, starches, gum acacia, calcium phosphate, alginates, liquid paraffin, calcium silicate, microcrystalline cellulose, polyvinyl pyrrolidone, cellulose, tragacanth, gelatin, syrup, methyl cellulose, methyl- and propyl-hydroxybenzoates, vegetable oils, such as olive oil, injectable organic esters such as ethyl oleate, talc, magnesium stearate, water and mineral oil. The formulations may also include wetting agents, lubricating, emulsifying and suspending agents, preserving agents, sweetening agents, perfuming agents, stabilizing agents or flavoring agents. The formulations of the invention may be formulated so as to provide quick, sustained or delayed release of the active ingredient after administration to the patient by employing procedures well-known in the art.

For oral administration, a compound of this invention, or a compound used in the methods of this invention, ideally can be admixed with carriers and diluents and molded into tablets or enclosed in gelatin capsules.

The compositions are preferably formulated in a unit dosage form, each dosage containing from about 1 to about 500 mg, more usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier, diluent or excipient therefor.

In order to more fully illustrate the operation of this invention, the following examples of formulations are provided. The examples are illustrative only and are not intended to limit the scope of the invention. The formulations may employ as active compounds any of the compounds of the present invention.

FORMULATION 1

Hard gelatin capsules suitable for use in treating Alzheimer's disease or reducing glucose concentration are prepared using the following ingredients:

|  | Amt. per Capsule | Concentration by Weight (percent) |
|---|---|---|
| Compound of Example No. 5 | 250 mg | 55.0 |
| Starch dried | 220 mg | 43.0 |
| Magnesium stearate | 10 mg | 2.0 |
|  | 460 mg | 100.0 |

The above ingredients are mixed and filled into hard gelatin capsules in 460 mg quantities.

FORMULATION 2

Capsules each containing 20 mg of medicament are made as follows:

|  | Amt. per Capsule | Concentration by Weight (percent) |
|---|---|---|
| Compound of Example No. 1 | 20 mg | 10.0 |
| Starch | 89 mg | 44.5 |
| Microcrystalline cellulose | 89 mg | 44.5 |
| Magnesium stearate | 2 mg | 1.0 |
|  | 200 mg | 100.0 |

The active ingredient, cellulose, starch and magnesium stearate are blended, passed through a No. 45 mesh U.S. sieve and filled into a hard gelatin capsule.

FORMULATION 3

Capsules each containing 100 mg of active ingredient are made as follows:

|  | Amt. per Capsule | Concentration by Weight (percent) |
|---|---|---|
| Compound of Example No. 45 | 100 mg | 29.0 |
| Polyoxyethylenesorbitan monooleate | 50 mcg | 0.02 |
| Starch powder | 250 mg | 71.0 |
|  | 250.05 mg | 100.02 |

The above ingredients are thoroughly mixed and placed in an empty gelatin capsule.

FORMULATION 4

Tablets each containing 10 mg of active ingredient are made up as follows:

| | Amt. per Capsule | Concentration by Weight (percent) |
|---|---|---|
| Compound of Example No. 71 | 10 mg | 10.0 |
| Starch | 45 mg | 45.0 |
| Microcrystalline cellulose | 35 mg | 35.0 |
| Polyvinyl pyrrolidone (as 10% solution in water) | 4 mg | 4.0 |
| Sodium carboxyethyl starch | 4.5 mg | 4.5 |
| Magnesium stearate | 0.5 mg | 0.5 |
| Talc | 1 mg | 1.0 |
| | 100 mg | 100.0 |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granule so produced is dried at 50°–60° C. and passed through a No. 18 mesh U.S. sieve. The sodium carboxymethyl starch, magnesium stearate and talc, previously passed through a No. 60 mesh U.S. sieve, are then added to the granule which, after mixing, is compressed on a tablet machine to yield a tablet weighing 100 mg.

FORMULATION 5

A tablet formula may be prepared using the ingredients below:

| | Amt. per Capsule | Concentration by Weight (percent) |
|---|---|---|
| Compound of Example No. 2 | 250 mg | 38.0 |
| Cellulose microcrystalline | 400 mg | 60.0 |
| Silicon dioxide fumed | 10 mg | 1.5 |
| Stearic acid | 5 mg | 0.5 |
| | 665 mg | 100.0 |

The components are blended and compressed to form tablets each weighing 665 mg.

FORMULATION 6

Suspensions each containing 5 mg of medicament per 40 ml dose are made as follows:

| | Per 5 ml of suspension |
|---|---|
| Compound of Example No. 59 | 5 mg |
| Sodium carboxymethyl cellulose | 50 mg |
| Syrup | 1.25 ml |
| Benzoic acid solution | 0.10 ml |
| Flavor | q.v. |
| Color | q.v. |
| Water | q.s. to 5 ml |

The medicament is passed through a No. 45 mesh U.S. sieve and mixed with the sodium carboxymethylcellulose and syrup to form a smooth paste. The benzoic acid solution, flavor and color is diluted with some of the water and added, with stirring. Sufficient water is then added to produce the required volume.

FORMULATION 7

An aerosol solution is prepared containing the following components:

| | Concentration by Weight (%) |
|---|---|
| Compound of Example No. 53 | 0.25 |
| Ethanol | 29.75 |
| Propellant 22 (Chlorodifluoromethane) | 70.00 |
| | 100.00 |

The active compound is mixed with ethanol and the mixture added to a portion of the propellant 22, cooled to −30° C. and transferred to a filling device. The required amount is then fed to a stainless steel container and diluted further with the remaining amount of propellant. The valve units are then fitted to the container.

We claim:

1. The compound 5-[[3,5-bis(1,1-dimethylethyl)-4-hydroxyphenyl)methylene]-4-oxo-2-thioxo-3-thiazolidine acetic acid or a pharmaceutically acceptable salt thereof.

2. A pharmaceutical formulation comprising a compound of claim 1 associated with at least one pharmaceutically acceptable carrier, diluent or excipient therefor.

3. The compound 5-[[3,5-bis(1-methylpropyl)-4-hydroxyphenyl)methylene]-4-oxo-2-thioxo-3-thiazolidine acetic acid or a pharmaceutically acceptable salt thereof.

4. A pharmaceutical formulation comprising a compound of claim 3 associated with at least one pharmaceutically acceptable carrier, diluent or excipient therefor.

5. The compound 5-[(3,5-dichloro-4-hydroxyphenyl)methylene]-2-thioxo-4-thiazolidinone or a pharmaceutically acceptable salt thereof.

6. A pharmaceutical formulation comprising a compound of claim 5 associated with at least one pharmaceutically acceptable carrier, diluent or excipient therefor.

7. The compound 5-[[3-ethoxy-4-hydroxy-5-(methylthiophenyl)phenyl]methylene]-4-oxo-2-thioxo-3-thiazolidine acetic acid or a pharmaceutically acceptable salt thereof.

8. A pharmaceutical formulation comprising a compound of claim 7 associated with at least one pharmaceutically acceptable carrier, diluent or excipient therefor.

9. The compound 5-[[3-(1,1-dimethylethyl]-4-hydroxy-5-(methylthiophenyl)phenyl]methylene]-2-thioxo-4-thiazolidinone or a pharmaceutically acceptable salt thereof.

10. A pharmaceutical formulation comprising a compound of claim 9 associated with at least one pharmaceutically acceptable carrier, diluent or excipient therefor.

11. The compound 5-[(3-ethoxy-4-hydroxyphenyl)methylene]-2-thioxo-3-methyl-4-thiazolidinone or a pharmaceutically acceptable salt thereof.

12. A pharmaceutical formulation comprising a compound of claim 11 associated with at least one pharmaceutically acceptable carrier, diluent or excipient therefor.

13. The compound 5-[(3-ethoxy-4-hydroxyphenyl)methylene]-2-thioxo-3-dimethylamino-4-thiazolidinone or a pharmaceutically acceptable salt thereof.

14. A pharmaceutical formulation comprising a compound of claim 13 associated with at least one pharmaceutically acceptable carrier, diluent or excipient therefor.

15. The compound 5-[[3-(1,1-dimethylethyl)-4-hydroxyphenyl]methylene]-2-thioxo-3-methyl-4-thiazolidinone or a pharmaceutically acceptable salt thereof.

16. A pharmaceutical formulation comprising a compound of claim 15 associated with at least one pharmaceutically acceptable carrier, diluent or excipient therefor.

* * * * *